US007766852B2

(12) United States Patent
O'Malley

(10) Patent No.: US 7,766,852 B2
(45) Date of Patent: Aug. 3, 2010

(54) NERVE TREATMENT APPARATUS

(75) Inventor: Jeanne O'Malley, 20370 Lorain Rd., Fairview Park, OH (US) 44126

(73) Assignee: Jeanne O'Malley, Fairview Park, OH (US)

( * ) Notice: Subject to any disclaimer, the term of this patent is extended or adjusted under 35 U.S.C. 154(b) by 589 days.

(21) Appl. No.: 11/676,968

(22) Filed: Feb. 20, 2007

(65) Prior Publication Data

US 2007/0225625 A1 Sep. 27, 2007

Related U.S. Application Data

(60) Provisional application No. 60/774,786, filed on Feb. 17, 2006.

(51) Int. Cl.
*A61F 5/00* (2006.01)

(52) U.S. Cl. .......................................... 602/32; 602/36

(58) Field of Classification Search .................. 602/32, 602/36, 40; 5/628, 630, 636, 640; 482/70, 482/101, 106
See application file for complete search history.

(56) References Cited

U.S. PATENT DOCUMENTS

| | | | | |
|---|---|---|---|---|
| 3,596,655 | A * | 8/1971 | Corcoran | 602/32 |
| 3,768,464 | A * | 10/1973 | Greissing | 602/32 |
| 3,868,951 | A * | 3/1975 | Albrecht | 602/32 |
| 4,781,372 | A * | 11/1988 | McCormack | 482/70 |
| 5,099,831 | A * | 3/1992 | Freed | 601/24 |
| 5,179,746 | A * | 1/1993 | Rogers | 5/625 |
| 5,317,771 | A | 6/1994 | Cook | |
| 5,669,859 | A * | 9/1997 | Liggett et al. | 482/94 |
| 5,797,153 | A * | 8/1998 | Amioka | 5/632 |
| 5,902,261 | A * | 5/1999 | Schwartz | 602/61 |
| 6,500,136 | B2 * | 12/2002 | Meyer | 602/18 |
| 7,060,046 | B2 * | 6/2006 | Tanaka et al. | 602/33 |
| 2003/0040686 | A1 | 2/2003 | Schaeffer | |
| 2003/0114780 | A1 | 6/2003 | Al-Obaidi et al. | |
| 2004/0171974 | A1 * | 9/2004 | Emsky | 602/33 |
| 2005/0261615 | A1 * | 11/2005 | Weston | 602/13 |
| 2008/0208089 | A1 * | 8/2008 | Newkirk et al. | 602/19 |

OTHER PUBLICATIONS

International Search Report and Written Opinion for International Application No. PCT/US2007/004550 dated Sep. 4, 2007.

* cited by examiner

*Primary Examiner*—Patricia M Bianco
*Assistant Examiner*—Victoria Hicks
(74) *Attorney, Agent, or Firm*—Renner, Otto, Boisselle & Sklar, LLP

(57) ABSTRACT

Nerve treatment/mobilization apparatuses are configured to mobilize a user's peripheral nervous system. The nerve treatment apparatus includes a back support, a pair of force applying members and a neck cradle. Additional optional attachments include upper body nerve mobilization tracks and a lower peripheral nerve mobilization device.

35 Claims, 14 Drawing Sheets

NERVE TREATMENT APPARATUS

RELATED APPLICATION DATA

This application claims priority of U.S. Provisional Application No. 60/774,786, filed on Feb. 17, 2006, which is incorporated herein by reference in its entirety.

TECHNICAL FIELD

The present invention relates generally to the field of physical therapy methods and apparatuses and, more particularly, to nerve mobilization and treatment apparatuses and methods.

BACKGROUND

Many activities in daily life require forward shoulder/forward head posture. Forward shoulder/forward head posture is or corresponds to the reversal of the normal spine curves. When normal spine curves are reversed for an extended period of time, for whatever reason, there may be consequences. One consequence is the eventual posture often associated with aging.

Nerve injury and the subsequent formation of neural scar tissue is prevalent among weight lifters, wrestlers, long distance bicycle riders and motorcycle riders, heavy equipment operators, especially pile drivers, and jobs requiring repetitive movement. The golf swing and tennis swing are also examples of repetitive motions that can injure a nerve. Nerve injuries generally do not respond to standard treatment such as ice and standard stretches. In fact, such standard treatments can actually worsen or exacerbate nerve injuries.

Upper Limb Tension Tests, which also may be referred to as Brachial Plexus Tension Tests or the Elvey Test are tension tests administered by a physical therapist to treat neurological structures and nerve injuries. Typically, the physical therapist administers the tension test with the user in a supine position. The therapist manipulates the user's arm to isolate, stretch and mobilize the injured nerves. These movements, however, are difficult to replicate without the aid of a physical therapist.

Typical stretching and other conventional physical therapy treatments may not alleviate pain caused by damage or injury to the lower peripheral nervous system. For example, some pain in the lower extremities, including knee and heel pain may not respond to other treatments.

Loss of hip extension (e.g., ability to move the leg backwards that frequently is accompanied, in more severe cases, by pain with initial rising from a chair or in the morning on initial standing) is a significant contributor to loss of movement in rotation of the body. Without hip extension, the rotation of the body is limited. Typically the affected person will do stretches in an attempt to regain lost movement. Stretches, however, are incapable of treating the source of the pain, if the pain is caused by a neural injury.

Often treatment focuses on treating an individual's muscles and joints without considering the impact of injury to the individual's nervous system.

SUMMARY

In view of the foregoing, a need exists for an apparatus and method of mobilizing an individual's peripheral nervous system.

One aspect of the disclose technology relates to a nerve treatment apparatus that includes a back support, a pair of force applying members that are configured to apply force to a user along predefined directions, and a neck cradle member movable with respect to the back support, the neck cradle member being configured to engage a user substantially adjacent the user's occiput and to facilitate retraction of the user's cervical spine.

According to another aspect, the pair of force applying members are configured to apply forces adjacent the user's anterior humeral heads According to another aspect, the pair of force applying members are configured to apply forces adjacent the user's anterior humeral heads, each of the force applying members being configured to apply a force in a direction having an angle of about 45 degrees with respect to the back support and an angle of about 45 degrees relative to a vertical plane that is perpendicular to the back support.

According to another aspect, the force applying members are configured to apply forces in directions along the user's lower trapezius muscle fibers.

According to another aspect, the force applying members are configured to apply forces effective to activate the user's lower trapezius muscles.

According to another aspect, the force applying members are configured to apply forces adjacent the user's anterior shoulder areas, each of the force applying members being configured to apply a force in a direction having an angle of about 45 degrees with respect to the back support and an angle of about 45 degrees relative to a vertical plane that is perpendicular to the back support.

According to another aspect, the force applying members are configured to apply forces substantially adjacent the user's anterior shoulder areas the forces being directed along an interior, posterior direction of about 45 degrees.

According to another aspect, the force applying members are movable with respect to the back support.

According to another aspect, the force applying members are configured to apply forces effective to facilitate cervical retraction in the user.

According to another aspect, the force applying members are configured to apply forces effective to direct the user's lower cervical curve into extension and the user's upper cervical curve into flexion.

According to another aspect, the force applying members are configured to apply forces effective to facilitate a posterior, inferior glide of the subject's scapulae.

According to another aspect, the force applying members are configured to apply forces in directions effective to facilitate movement of the user's scapulae in a retracted inferior glide.

According to another aspect, the force applying members are configured to intermittently apply forces to the user along predefined directions.

According to another aspect, the force applying members are configured to automatically apply forces to the user adjacent the user's anterior should area along predefined directions.

According to another aspect, the force applying members are operatively coupled to a motor and a motor control, such that the force applying members are operative to automatically apply force to the user along predefined directions.

According to another aspect, the apparatus includes at least one motor operatively coupled to the force applying members, a motor controller for controlling the at least one motor and a data entry module configured to receive data relating to the user.

According to another aspect, the data entry module is configured to receive data relating a the user's height, weight, age and/or physical condition.

According to another aspect, the force applying members and neck cradle are height-adjustable.

According to another aspect, the force applying members are driven intermittently via an actuation mechanism.

According to another aspect, the back support is configured to direct the user's lumbar spine into extension.

According to another aspect, the back support includes a lumbar roll member.

According to another aspect, the apparatus includes a fixation member configured to cooperate with the back support to retain the user's pelvis against the back support.

According to another aspect, the apparatus includes a hip support configured to retain the user's pelvis against the back support.

According to another aspect, the apparatus includes a retention member configured to engage the user's anterior iliac crests and to retain the user against the back support.

According to another aspect, the apparatus includes a lumber extension device configured to cooperate with the back support to direct the user's lumbar spine into extension.

According to another aspect, the lumbar extension device comprises a lumbar support member coupled to the back support and a pelvis retention member configured to releasably engage the user's anterior iliac crests.

According to another aspect, the apparatus includes a safety release mechanism operable to trigger release of force applying members.

According to another aspect, the safety release mechanism includes a release trigger device operable by the user.

According to another aspect, one or more force sensors operable to sense force and operable to trigger release of the force applying members and the fixation device and the neck cradle upon sensing of predefined force.

According to another aspect, the apparatus includes at least one nerve mobilization track operatively coupled to the back support.

According to another aspect, the nerve mobilization track is a radial nerve mobilization track.

According to another aspect, the nerve mobilization track is a median nerve mobilization track.

According to another aspect, the nerve mobilization track is an ulnar nerve mobilization track.

According to another aspect, the at least one nerve mobilization track includes a radial nerve mobilization track, a median nerve mobilization track and an ulnar nerve mobilization track.

According to another aspect, the apparatus includes a lower body slider that is movable in a direction substantially perpendicular to the back support.

According to another aspect, the lower body slider is configured to slide on at least one slider track.

According to another aspect, the lower body slider includes a lower body cradle.

Another aspect relates to a nerve mobilization apparatus that includes a back support and at least one upper body nerve mobilization track operatively coupled to the back support.

According to another aspect, the apparatus includes a user-engageable implement that is movable along the upper body nerve mobilization track.

According to another aspect, the apparatus includes a guide member that is movable along the upper body nerve mobilization track.

According to another aspect, the apparatus includes a gripping implement that is movable along the upper body nerve mobilization track.

According to another aspect, the nerve mobilization track is a radial nerve mobilization track.

According to another aspect, the radial nerve mobilization track is configured to provide resistance to a user's pectoralis major and latissimus dorsi muscles followed by passive recoil into a radial nerve glide.

According to another aspect, the nerve mobilization track is a median nerve mobilization track.

According to another aspect, the median nerve mobilization track is configured to provide resistance to a user's biceps brachii and brachialis muscles followed by passive recoil into a median nerve glide.

According to another aspect, the nerve mobilization track is an ulnar nerve mobilization track.

According to another aspect, the ulnar nerve mobilization track is configured to provide resistance to a user's wrist flexors and triceps muscles followed by passive recoil into an ulnar nerve glide.

According to another aspect, the at least one upper body nerve mobilization track includes a radial nerve mobilization track, a median nerve mobilization track and an ulnar nerve mobilization track.

According to another aspect, the apparatus includes a pair of force applying members that are configured to apply forces to a user along predefined directions, and a neck cradle member movable with respect to the back support, the neck cradle member being configured to engage a user substantially adjacent the user's occiput and to facilitate retraction of the user's cervical spine.

According to another aspect, the force applying members are configured to apply forces adjacent the user's anterior humeral heads.

According to another aspect, the back support is configured to direct the user's lumbar spine into extension.

According to another aspect, the back support includes a lumbar roll member.

According to another aspect, the apparatus includes a hip support configured to retain a user's pelvis against the back support.

Another aspect relates to a lower peripheral nerve mobilization apparatus that includes a back support and a lower body slider configured to engage a portion of a user's lower body, the lower body slider being movable in a direction substantially perpendicular to the back support.

According to another aspect, the apparatus includes at least one slider track, wherein the lower body slider is configured to slide on the at least one slider track.

According to another aspect, the lower body slider includes a lower body cradle configured to engage a portion of the user's lower body.

According to another aspect, the apparatus includes a pair of force applying members that are configured to apply forces to a user along predefined directions, and a neck cradle member movable with respect to the back support, the neck cradle member being configured to engage a user substantially adjacent the user's occiput and to facilitate retraction of the user's cervical spine.

According to another aspect, the force applying members are configured to apply forces adjacent the user's anterior humeral heads.

According to another aspect, the back support is configured to direct the user's lumbar spine into extension.

According to another aspect, the apparatus includes at least one upper body nerve mobilization track operatively coupled to the back support.

According to another aspect, the upper body nerve mobilization track is a radial nerve mobilization track.

According to another aspect, the upper body nerve mobilization track is a median nerve mobilization track.

According to another aspect, the upper body nerve mobilization track is an ulnar nerve mobilization track.

According to another aspect, the at least one upper body nerve mobilization track includes a radial nerve mobilization track, a median nerve mobilization track and an ulnar nerve mobilization track.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended thereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Likewise, elements and features depicted in one drawing may be combined with elements and features depicted in additional drawings. Moreover, in the drawings, like reference numerals designate corresponding parts throughout the several views.

DETAILED DESCRIPTION

Figure 1:
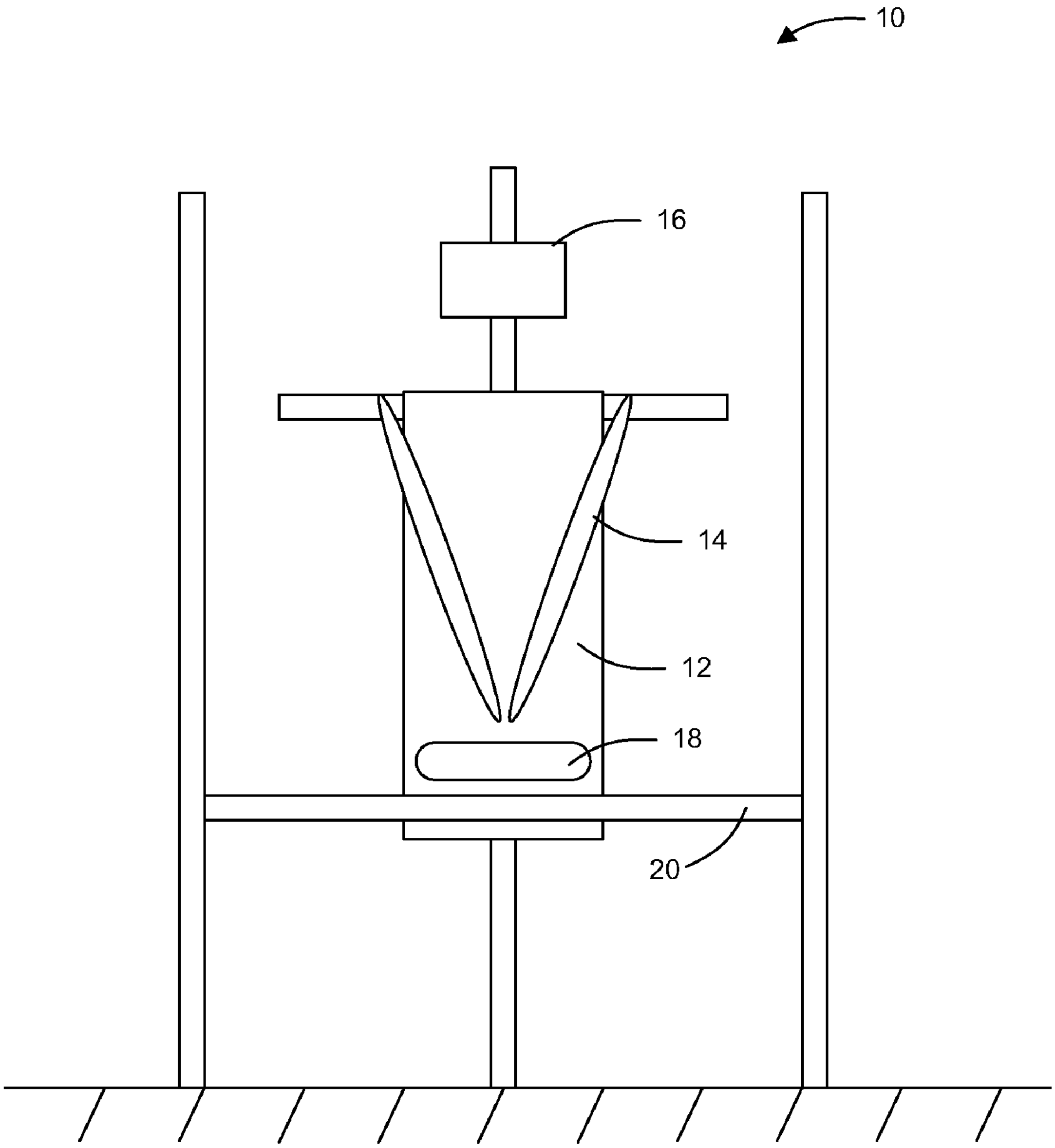
FIG. 1 is a diagrammatic illustration of a nerve treatment apparatus in accordance with one exemplary embodiment.

In the detailed description that follows, like components have been given the same reference numerals regardless of whether they are shown in different embodiments of the present invention. To illustrate the present invention in a clear and concise manner, the drawings may not necessarily be to scale and certain features may be shown in somewhat schematic form.

Aspects of the disclosed technology relate to a nerve treatment/mobilization apparatus or multiple nerve treatment/mobilization apparatuses that are configured to mobilize the user's peripheral nervous system. In some disclosed embodiments, the nerve treatment apparatus or multiple nerve treatment apparatuses are configured to mobilize the user's peripheral nervous system while concurrently addressing the curves of the user's spine. One or more of the disclosed nerve treatment apparatuses may be employed to train and/or treat a user with respect to sports-related motion. Additionally or alternatively, one or more of the disclosed nerve treatment apparatuses may be employed to train and/or treat a user with respect to work-related motion.

As will be understood from the present disclosure, other aspects of the disclosed technology relate to methods of training and treating a subject to improve sports-related motion; methods of training and treating a subject to improve work-related motion; methods of treating/preventing chronic pain; methods of treating/correcting forward shoulder and/or head posture; methods of treating pain related to a variety of ailments and injuries (e.g., burn-related injury, head injuries, etc.); method of increasing a subject's oxygen intake (improving a subject's vital capacity).

While for purposes of simplicity of explanation, apparatuses illustrated in FIGS. 1-25 include a variety of elements, components, assemblies, members or integers that that represent one or more aspects of the relevant operation of the disclosed nerve mobilization apparatus(es), it is to be understood and appreciated that aspects of the invention described herein are not limited to the exact configuration of disclosed elements, components, assemblies, members or integers, as some elements, components, assemblies, members or integers may, in accordance with aspects of the present invention, occur in different orders and/or concurrently elements, components, assemblies, members or integers from that shown or described herein. Moreover, not all illustrated elements, components, assemblies, members or integers of aspects of the disclosed nerve mobilization apparatus(es) must be present in a single embodiment in accordance with an aspect of the invention. Further, features, elements, components, assemblies, members or integers that are described and/or illustrated with respect to one embodiment may be used in the same way or in a similar way in one or more other embodiments and/or in combination with or instead of the features of the other embodiments.

Referring now to FIGS. 1-7 a nerve treatment apparatus 10 (also referred to as a nerve mobilizer, a nerve mobilization apparatus or the like) includes a back support 12, a pair of force applying members 14, and a neck cradle member 16. As is discussed below, the force applying members 14 and the neck cradle cooperate to guide the user's cervical spine into a retracted position while guiding the user's shoulders into a posterior, inferior glide, e.g., allowing the user's scapulae to retract and depress, for example, in a "V" movement direction. In one embodiment, the back support 12 is oriented substantially vertically, and is configured to support a user of the nerve treatment apparatus 10. Optionally, the nerve treatment apparatus may be configured such that the user is disposed substantially horizontally.

In a preferred embodiment, the back support is configured to support the user's back while directing or otherwise facilitating the user's lumbar spine into extension (which also may be thought of as directing or otherwise facilitating the user's lumbar spine into its correct direction). In one embodiment, the back support 12 includes or is otherwise operatively coupled to a lumbar extension member 18, e.g., a lumbar roll member. The lumbar extension member 18 may be formed integrally with the back support 12 or, alternatively, the lumbar extension member may be configured as an attachment to the back support 12.

The nerve treatment apparatus also may include a pelvis fixation member or members 20 (also referred to as a hip support or hip supports) that are configured to cooperate with the back support 12 to retain or otherwise support the user's pelvis or hips against the back support 12. Stated differently, the pelvis fixation member or members 20 may be configured to engage the user's anterior iliac crests to retain or otherwise support the user against the back support 12. It will be appreciated that the combination of a back support, equipped with or otherwise operatively coupled to a lumber extension member and a pelvis fixation member, will be effective to facilitate lumbar spine extension for a user of the nerve treatment apparatus.

The force applying members 14, which are movable with respect to the back support 12, are configured to apply predefined forces along predefined directions to the user of the nerve treatment apparatus. In a preferred embodiment, the force applying members are configured to engage or otherwise contact the anterior of the user in an areas adjacent the user's anterior shoulders, e.g., in an areas adjacent the user's anterior humeral heads. In one embodiment, each of the force applying members is configured to apply a force in or along a direction having an angle of about 45 degrees with respect to the back support 12 and an angle of about 45 degrees with respect or relative to a plane, e.g., a vertical plane, that is substantially perpendicular to the back support 12. Stated differently and in accordance with another embodiment, each of the force applying members is configured to apply a force in or along a direction having an angle of about 45 degrees with respect to the back support and an angle of about 45 degrees with respect to the user's spine.

Stated in yet another way and in accordance with another embodiment, each of the force applying members is configured to apply forces substantially adjacent the user's anterior humeral heads along an interior, posterior direction of about 45 degrees. Stated in yet another way and in accordance with another embodiment, each of the force applying members is configured to apply forces substantially adjacent the user's anterior humeral heads in or along directions effective to facilitate movement of the user's scapulae in a posterior, inferior glide (also referred to as a retracted inferior glide). Stated in yet another way and in accordance with another embodiment, the force applying members are configured to apply forces in directions along the user's lower trapezius muscle fibers (this may also be thought of as activating the user's lower trapezius muscles).

While aspects of the nerve treatment apparatus are being described with respect to force applying members that, in one embodiment, are configured to apply forces in or along directions having angles of about 45 degrees with respect to the back support and about 45 degrees with respect to the user's spine, it will be appreciated that the force applying members may be configured to apply forces to the user at angles different than 45 degrees (e.g., at angles of about 40 to about 50 degrees or larger or smaller angles) provided that the angles at which the forces are applied are effective to facilitate movement of the user's scapulae in a retracted, inferior glide.

Figure 2:
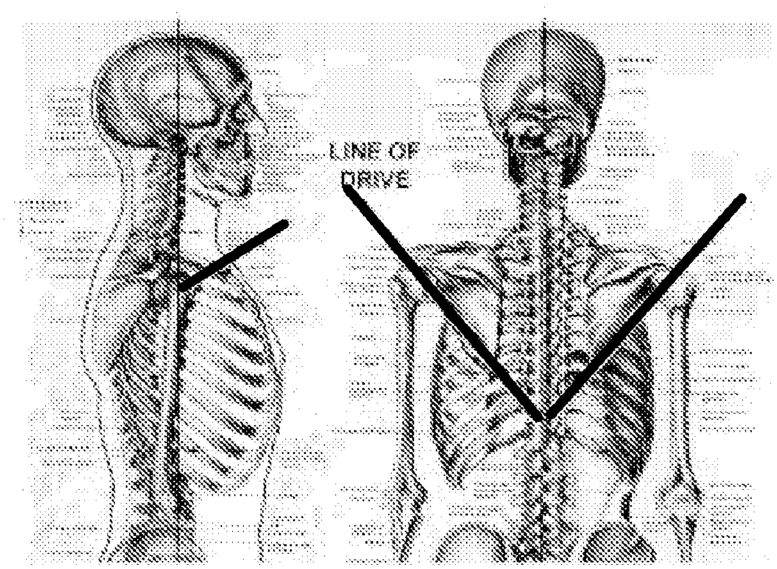
FIG. 2 is a diagrammatic illustration showing predefined directions along which the exemplary nerve treatment apparatus applies forces to a user.

FIG. 2 presents an exemplary illustration of the preferred directions along which the force applying members apply force to the user's anterior shoulder area (this direction or directions may also be referred to as the line of drive).

Figure 3:
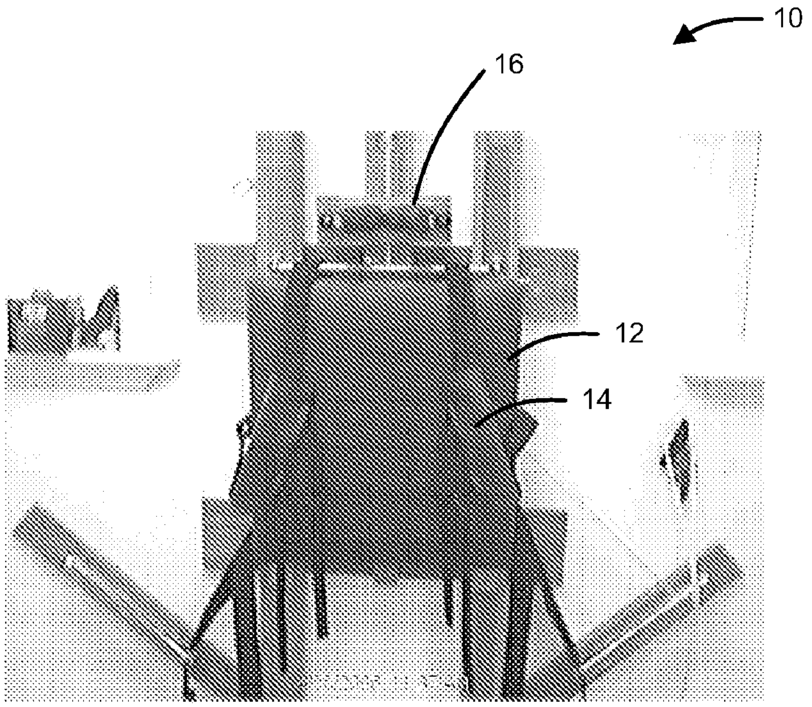
FIG. 3 is a diagrammatic illustration of an exemplary nerve apparatus.
Figure 4:
FIG. 4 is a perspective view of the exemplary nerve apparatus shown in FIG. 3.

It will be appreciated that the force applying members may take on a variety of configurations without departing from the scope of the present invention. For example, as shown in FIG. 1 and FIGS. 3 and 4, the force applying members 14 may be configured as shoulder straps or other strap-like members, which may be actuated manually, semi-automatically or automatically to provide or otherwise apply predefined forces along the above-described predefined direction or directions to facilitate the desired of the user's shoulder area. In the embodiment, illustrated in FIGS. 1, 3 and 4, the force applying members are connected or otherwise anchored behind the user (such that the force applying members apply predefined forces along predefined directions by pulling on the user when actuated).

Figure 5:
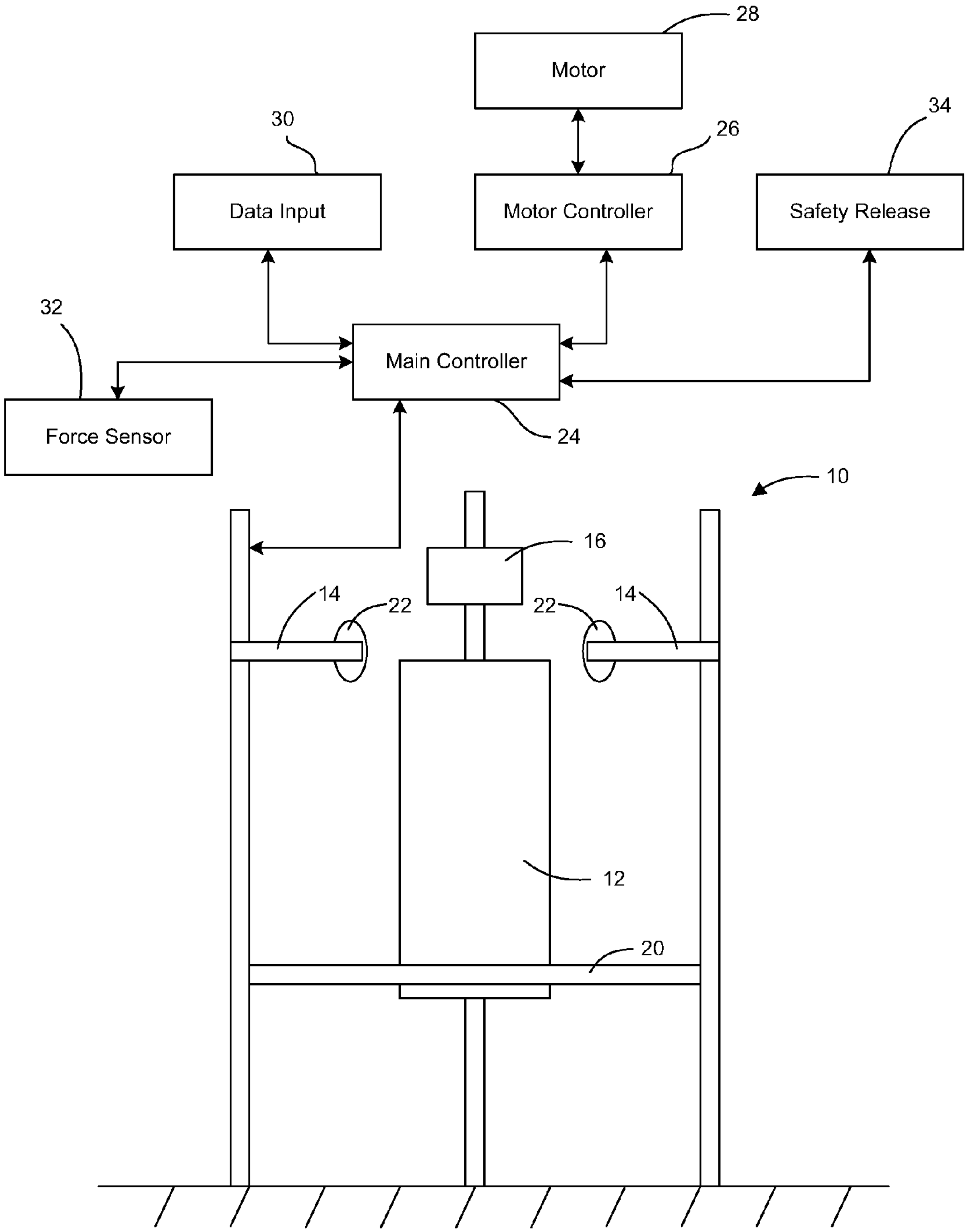
FIG. 5 is a diagrammatic illustration of an exemplary automated nerve treatment apparatus.
Figure 6:
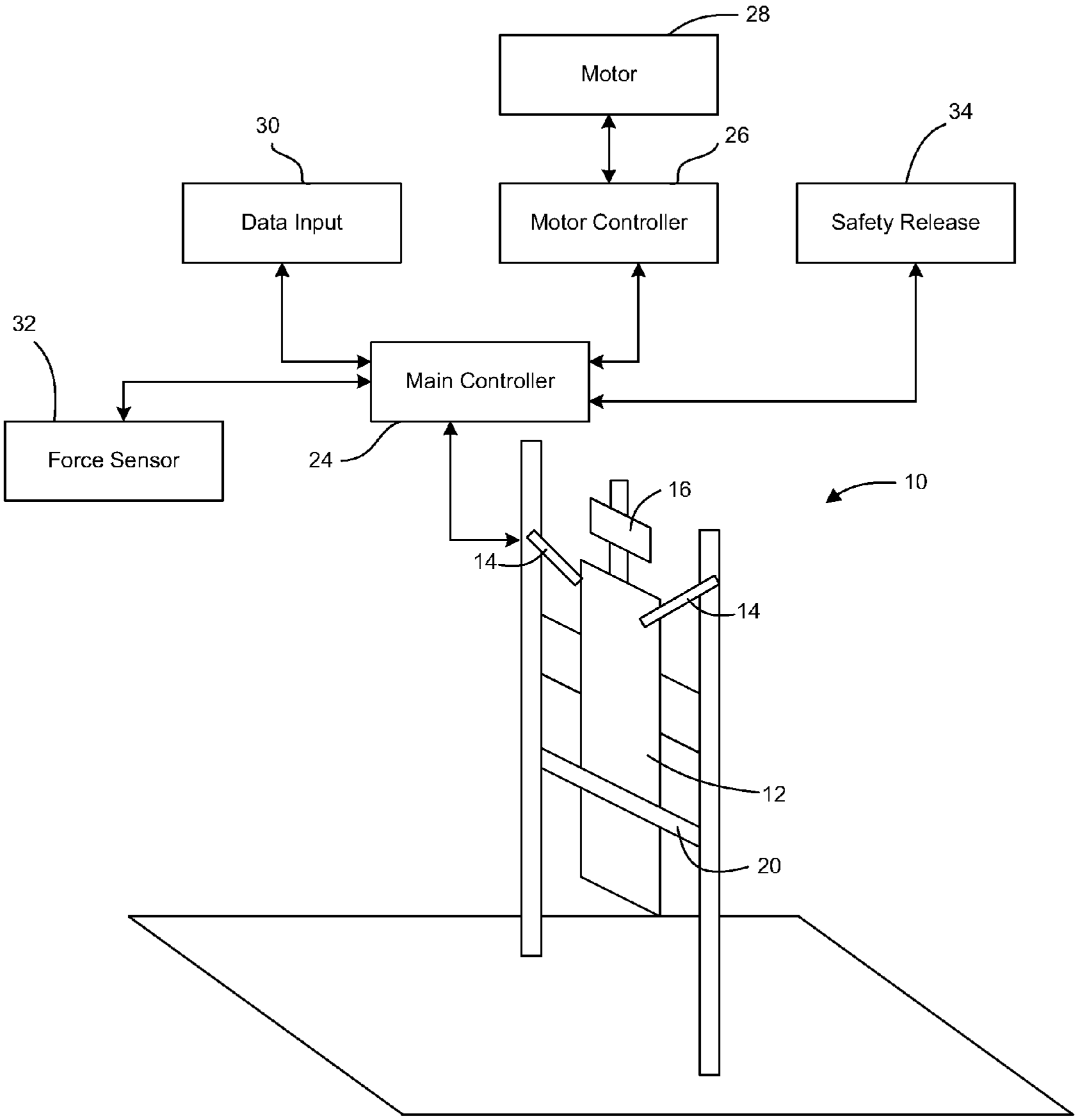
FIG. 6 is a diagrammatic illustration of an exemplary automated nerve treatment apparatus.
Figure 7:
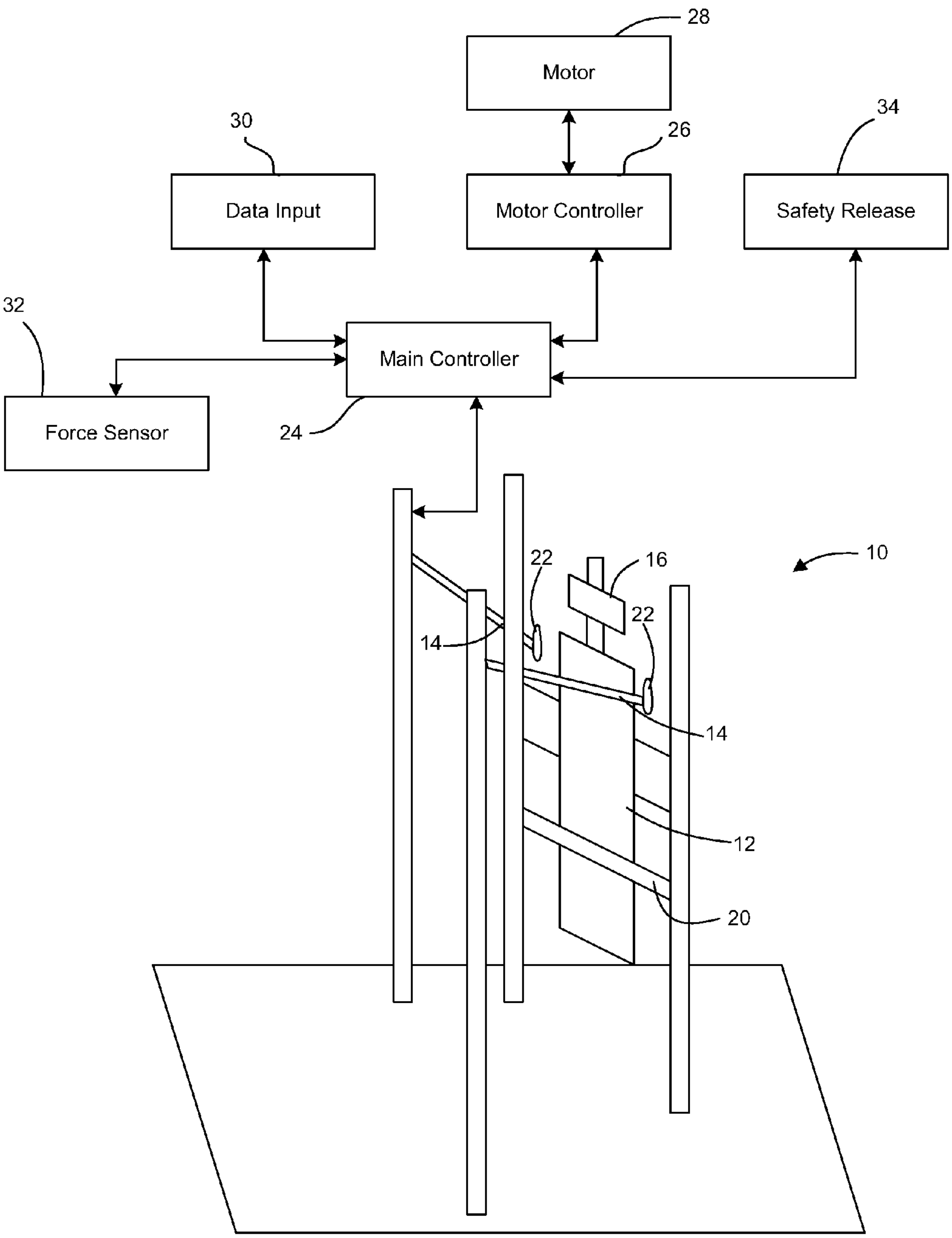
FIG. 7 is a diagrammatic illustration of an exemplary automated nerve treatment apparatus.

Alternatively, the force applying members 14 may take on any other suitable configuration without departing from the scope of the present invention. For example, as is shown in FIGS. 5-7, the force applying members 14 may be embodied as force applying arms that are telescoping or otherwise operatively connected to support structures 22 for applying to the user the predefined forces in predefined directions, for example, once the user steps into the nerve treatment apparatus (such as when the user places his/her back in contact with the back support). As is illustrated schematically in FIG. 7, the force applying members 14 may include suitably configured pads for applying to the user the desired predefined forces in predefined directions. For example, the pads may be curved or otherwise formed to have a shape configured to substantially conform the anterior shoulder areas of the user. In addition or alternatively, the nerve treatment apparatus may be equipped with multiple pads of different sizes and shapes to accommodate the physiques of different users.

In addition, as is shown schematically in FIGS. 5-7, the nerve treatment apparatus 10 may be configured as an automatic apparatus, e.g., an apparatus where suitable forces are applied automatically upon entry of processing of patient-specific data or upon suitable setting of such force parameters by a user or professional administering treatment using the device. As in the manual embodiment, the nerve treatment apparatus is configured to be height adjustable, e.g., automatically adjusting the appropriate height for a user upon receipt of user data. Suitable automation devices and/or circuitry may include a main controller 24 that controls the overall operation of the nerve treatment apparatus 10. A motor controller 26, which is coupled to one or more motors 28, may serve to operate the motor(s) in a way such that the force applying members 14 controllably apply the predefined forces in the predefined directions to the user of the nerve treatment apparatus. In addition, the nerve treatment apparatus may be equipped with a data input module 30, e.g., a keypad, keyboard, touch screen or the like, that is configured to accept data input indicative of one or more of the user's vital statistics, e.g., the user's height, the user's weight, the user's age, the user's physical condition and the like. It will be appreciated that this data may be entered by a professional, who is administering treatment using the nerve treatment apparatus (e.g., a physical therapist), or by the user himself/herself.

Preferably, the nerve treatment apparatus will include a force sensor or sensors 32 and suitable safety release mechanisms 34. The apparatus may be configured such that the force sensors 32 sense the various forces being applied to the user and, conversely, forces exerted or applied by the user to the various components of the nerve treatment apparatus. For example, force sensors may be incorporated into the force applying members, e.g., into the pads attached to the force applying members, into the neck cradle, into the pelvis fixation member, into the back support and the like. Upon detection of a force that is beyond the scope of predetermined permissible forces, either being applied to the user by the nerve treatment apparatus or being exerted or applied by the user to the nerve treatment apparatus, the nerve treatment apparatus may trigger a safety release, whereby the user is automatically released from the device, e.g., the force applying members automatically disengage or release from applying force to the user, the neck cradle automatically releases and the pelvis fixation member automatically releases.

In addition, it will be appreciated that any other nerve mobilization apparatus or attachments may be released as well upon triggering of the safety release mechanism. Alternatively or additionally, the nerve treatment apparatus may include a user-activatable safety release mechanism, whereby actuation of the safety release actuator by the user results in automatic release of all components of the nerve treatment apparatus, e.g., all components of the nerve treatment apparatus will release from applying forces to or otherwise restraining the user of the apparatus. It will be appreciated that aspects of the invention are not limited to the particulars of the type of motor, motor controller, data input module, force sensor(s), safety release mechanism(s) or the like.

The neck cradle 16, which is movable with respect to the back support 12 is configured to engage a user, e.g., substantially adjacent the user's occiput, to facilitate retraction of the user's cervical spine, preferably, concurrently with the applying of forces by the force applying members 14. While the neck cradle may take on any suitable configuration, the neck cradle should be operable to engage the user's occiput, for example, at the external occipital protuberance and the occipital condyles. Preferably, the neck cradle will be configured such that it cannot or will not reach or otherwise engage the condylar process of the user's mandible. In one embodiment, the neck cradle facilitates retraction of the user's cervical spine by engaging the user, e.g., substantially adjacent the user's occiput, and moving upward in a controlled manner over a predetermined distance.

In operation, the nerve treatment apparatus will facilitate the cervical and lumbar spine curves into their correction direction, thereby restoring the normal range of motion of these curves to their maximum potential. The cervical spine may be guided into a retracted position by the neck cradle. As is discussed above with respect to operation of the force applying members, it will be appreciated that the neck cradle also may be operated in an automated fashion, e.g., in connection with one or more of the main controller 24, the motor controller 26, the motor(s) 28, the data input module 30, the sensor(s) 32 and the safety release mechanism(s) 34. Concurrently, the shoulders may be guided by the force applying members into a posterior, inferior glide allowing the user's scapulae to retract and depress, e.g., in a "V" movement direction. The lumbar spine, which may be supported by a lumbar extension member disposed at the lumbar curve and supports at the anterior iliac crests, preventing the pelvis from moving forward away from the device, is moved into the direction of extension or, in the case of limited or no loss of lumbar spine extension, to direct the lumbar spine into its maximum amount of normal extension.

In a preferred embodiment, the nerve treatment apparatus is configured to intermittently apply force, both via the force applying members and by the neck cradle in a rhythmic "pressure-on-pressure-off" manner with the appropriate amount of force to the user's anterior shoulders and occipital area.

With unacceptable pressure forces, e.g., preprogrammed into the main controller and/or safety release mechanism, the nerve treatment apparatus will automatically power off, thereby providing release of the force applying members, the neck cradle and the hip supports. Of course, a user-activatable safety release mechanism, such as a suitable button or switch, may be held by the user, whereby the user may activate the safety release mechanism upon the onset of any pain or discomfort. Other attachments for the above-described nerve treatment apparatus 10 will be discussed below. It will be appreciated that each nerve treatment apparatus described in this disclosure may stand alone as a separate device or, may be linked together to form a single nerve treatment apparatus capable of providing all of the functionality described herein, e.g., mobilization of the user's entire peripheral nervous system.

Referring now to FIGS. 8-14, an upper body nerve treatment apparatus 50 (also referred to as an upper body nerve mobilizer, an upper body peripheral nerve mobilizer, an arm and shoulder mobilizer, or an upper body nerve treatment attachment or component) is disclosed. As is discussed below, the upper body nerve treatment apparatus is effective to mobilize peripheral nerves of a user's upper body by facilitating the administration of tension tests and by mobilizing the ulnar, radial, and median nerves in the upper extremities.

Figure 8:
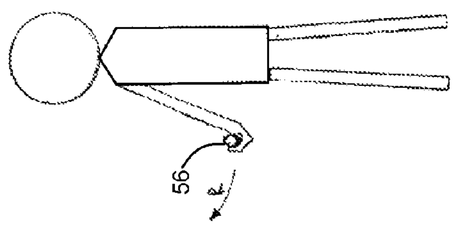
FIG. 8 is a diagrammatic illustration of a trajectory used to mobilize the radial nerve.
Figure 9:
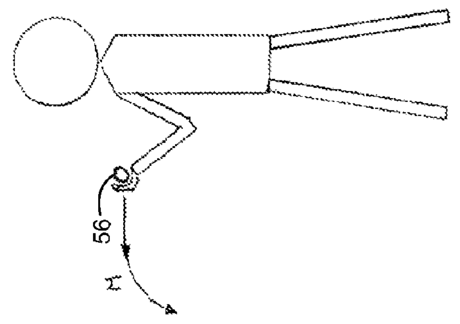
FIG. 9 is a diagrammatic illustration of a trajectory used to mobilize the median nerve.
Figure 10:
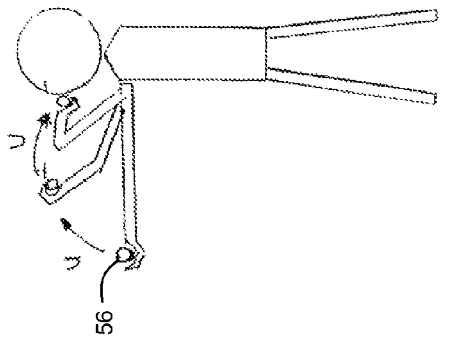
FIG. 10 is a diagrammatic illustration of a trajectory used to mobilize the ulnar nerve.

With initial reference to FIGS. 8-10, the general trajectories facilitated by the upper body nerve treatment apparatus for mobilizing the radial, median and ulnar nerves are shown. The ulnar nerve is mobilized by moving the arm along the general trajectory labeled U. Similarly, the median nerve is mobilized by moving the arm along trajectory M, and the radial nerve is mobilized by moving the arm along trajectory R. For the mobilization of each nerve, the user's movements are guided or otherwise facilitated by the upper body nerve treatment apparatus, e.g., via a mobilization track or other trajectory guide, which guides, steers or otherwise facilitates the movement of the user's arm along the proper trajectory for mobilizing the desired nerve, as described in more detail below. The movement guided or facilitated by each mobilization track or trajectory isolates and glides the user's upper body, e.g., the user's arm, to achieve mobilization of the targeted nerve. The guide may be a handle or other gripping implement slidable or otherwise movable along or within each mobilization track along each trajectory, as described with respect to FIG. 11 below.

Figure 11:
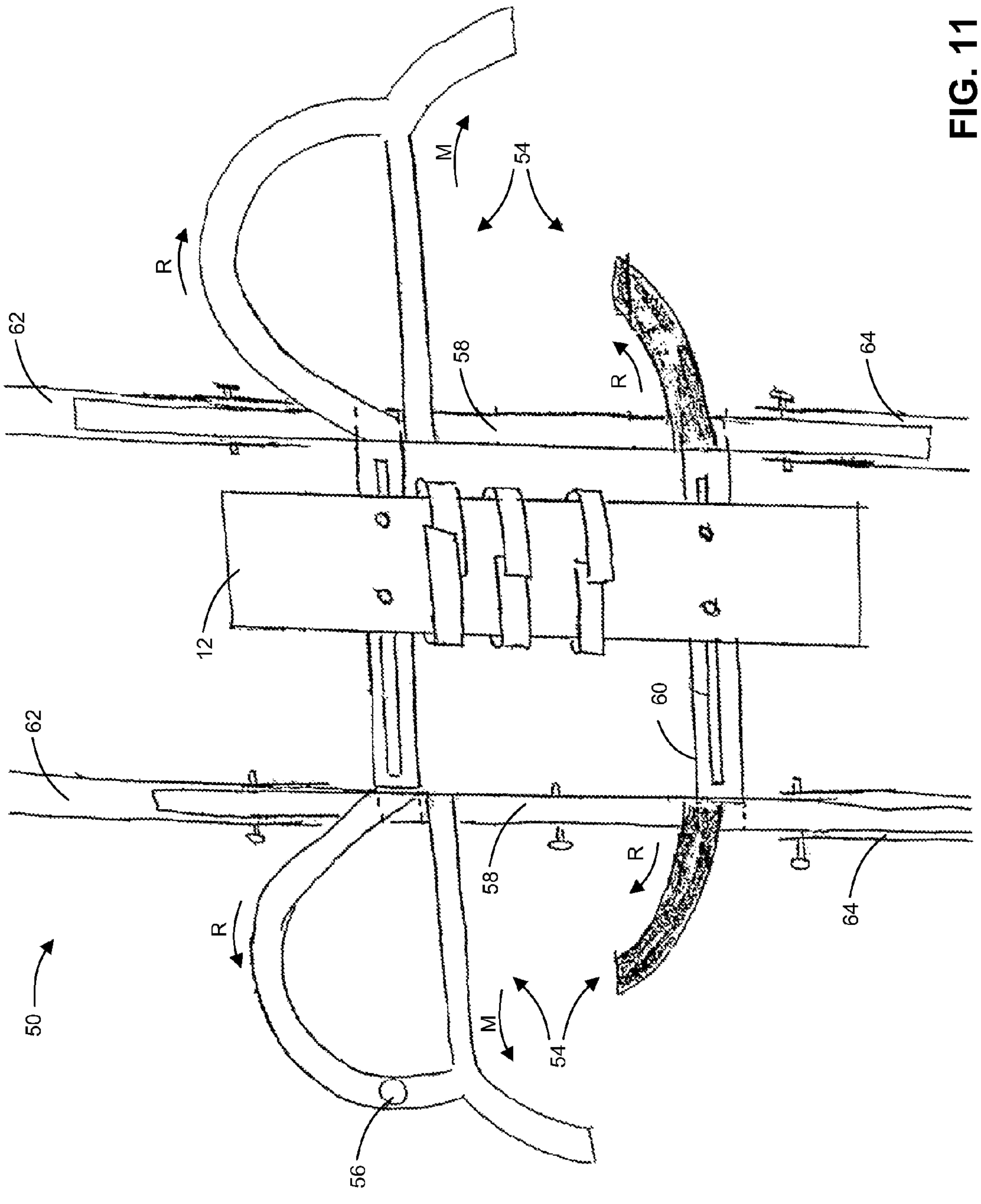
FIG. 11 is a diagrammatic illustration of an upper body nerve treatment apparatus in accordance with an exemplary embodiment.

The mobilization of the radial nerve is illustrated generally by FIG. 8. The gripping implement 56 slides or otherwise is movable along a nerve mobilization track that follows radial nerve trajectory R (FIG. 11). The radial nerve mobilization trajectory is a generally circular or arc-shape. The user mobilizes the radial nerve by grasping the handle 56 with the arm straight, e.g., next to the user's side and the palm facing outward or away from the user's body. The user then moves the handle along the radial nerve trajectory R, away from the user's body. As the user moves along the radial nerve mobilization trajectory R, the upper body nerve apparatus optionally offers resistance to the pectoralis major and latissimus dorsi muscles followed by passive recoil into a radial nerve glide. This general motion along radial nerve trajectory R can be coupled with inward or outward resistance and can be repeated several times to mobilize the radial nerve and radial nerve pathway while simultaneously strengthening the surrounding musculature.

The mobilization of the median nerve is illustrated generally by FIG. 9. The user initially grasps the handle 56 with the arm bent, e.g., with the elbow near the user's side, and the palm facing upward. The handle 56 slides or is otherwise movable along a track that follows medial nerve trajectory M. The medial nerve trajectory is generally horizontal and downwardly curved such that the user's arm is fully extended with the palm facing away from the user's body and the wrist fully flexed. The median nerve mobilizer optionally offers resistance to the biceps brachii, the long and short heads, and the brachialis muscles followed by passive recoil into a median nerve glide. This general motion along medial nerve trajectory M can be coupled with inward or outward resistance and repeated several times to mobilize the medial nerve and medial nerve pathway, while simultaneously strengthening the surrounding musculature.

Referring to FIG. 10, the mobilization of the ulnar nerve generally begins with the arm extended and substantially parallel to the ground. The user grasps the handle 56 with the palm of the hand facing downward. The handle 56 slides or is otherwise movable along the ulnar nerve trajectory U, which is a generally curved shape. At the end of the movement, the user's arm is in a position with the elbow bent with the hand at or near the user's ear (e.g., near the top of the shoulder). This movement is generally depicted by the ulnar nerve trajectory U. The ulnar nerve mobilizer offers resistance to the wrist flexors and triceps muscles followed by passive recoil into an ulnar nerve glide. This general motion along ulnar nerve trajectory U can be coupled with inward or outward resistance and can be repeated several times to mobilize the ulnar nerve and ulnar nerve pathway, while simultaneously strengthening the surrounding musculature.

It will be appreciated that while the above trajectories are described with respect to certain beginning and ending points other variations are possible. The particular beginning and end points are illustrative only of locations where the user can begin and end the particular mobilizations. In addition, aspects of the herein describe upper body nerve treatment apparatus are not limited to resistance and/or recoil in particular directions (e.g., outward resistant and passive inward recoil or inward resistant and passive outward recoil).

Referring now to FIG. 11, an exemplary embodiment of the arm and shoulder mobilizer 50 is shown. The mobilizer 50 may be mounted to a wall or may be a stand-alone unit. In one preferred embodiment, the arm and shoulder mobilizer 50 is configured to be integral with or otherwise operatively coupled to the nerve treatment apparatus 10 described above with respect to FIGS. 1-7. In one embodiment, the nerve treatment apparatus includes a main support 12, e.g., a back support, that supports the user's back and facilitates, restores and/or increases the lower cervical and/or lumbar spine extension by restoration of the spine curves. As is described above with respect to FIGS. 1-7, the back support may include or otherwise be operatively coupled to a lumbar extension member, e.g., a lumbar roll member. The lumbar extension member may be formed integrally with the back support 12 or, alternatively, the lumbar extension member may be configured as an attachment to the back support 12.

The back support may also include or otherwise cooperate with one or more hip supports that are configured to cooperate with the back support 12 to retain or otherwise support the user's pelvis or hips against the back support 12. Stated differently, the hip supports may be configured to engage the user's anterior iliac crests to retain or otherwise support the user against the back support 12. It will be appreciated that the combination of a back support, equipped with or otherwise operatively coupled to a lumber extension member and a pelvis fixation member, will be effective to facilitate lumbar spine extension for a user of the nerve treatment apparatus.

As is described above with respect to FIGS. 1-7, the main support may be operatively coupled to or otherwise associated with a pair of force applying members, such as, for example, straps or belts or force-applying arms that pull or push the shoulders in the direction of the thoracic muscles, as described above with respect to the nerve treatment apparatus 10. The support or force in the direction of the thoracic muscles also may be provided by an electronically controlled device, such as a hydraulic piston or otherwise as will be appreciated by one of skill in the art.

The back support is operatively coupled to one or more nerve mobilization tracks (labeled generally as mobilization tracks 54). The nerve mobilization tracks are coupled to one or more handles or user gripping implements. The nerve mobilization tracks are configured to facilitate mobilization of the ulnar, medial and radial nerve(s) by guiding the user through movements along the mobilization trajectories U, R, M when the user is disposed with his/her back against the back support and while gripping the handle.

In the particular embodiment of FIG. 11, the back support 12 is generally planar and comprised of two vertical members 58 and two horizontal members 60, which are mounted or attached to one another via a weld, bolt, or other securing mechanism. Upper and lower sleeves or tracks are used in conjunction with the vertical members to facilitate adjustment of the height of the back support. The upper and lower sleeves receive a portion of the vertical members 58 for the vertical adjustment. Alternatively, the entire arm and shoulder nerve mobilizer may be automated, allowing for automatic height adjustment upon receipt of data associated with the particular user.

In one embodiment, the upper sleeve 62 and lower sleeve 64 are hollow tubes or track-like members into which or on which the vertical members 58 may slide. The base can then be slid to a higher or lower level to accommodate taller or shorter users by sliding the vertical members 58 within the upper and lower sleeves 62, 64 and securing them at the desired height with any conventional securing mechanism, e.g., pins, rivets, pegs, screws or the like. It will be appreciated by one of skill in the art that although illustrated as vertically slidable via two vertical supports, a single support or other sliding mechanism may be used. Alternatively, the sleeves may be tracks that slidably engage the vertical members, or another variation as will be appreciated by one of skill in the art.

The back support 12 may be adjustable to the left or right to allow users having different arm lengths to use the arm and shoulder mobilizer 50. The horizontal members 58 have a track and a sliding mechanism that fits within or onto the track to allow the user to slide the back support horizontally. As shown, the back support may be movable on each of the two horizontal members via sliding members. In an exemplary embodiment, the upper sliding members are slidably engaged to the upper horizontal member 60 via the track 60 and the lower sliding mechanisms are slidably engaged to the lower horizontal member in substantially the same manner. Once moved into the desired position, the sliding mechanisms can be locked to the horizontal members to prevent any further movement by a bolt or other conventional securing mechanism. It will be appreciated by one of skill in the art that the multiple sliding mechanisms or a single sliding mechanism may be provided for sliding the base to the left and right.

In another embodiment, the vertical and horizontal adjustments are achieved electronically by programming a controller, e.g., the main controller described above with respect to FIGS. 5-7, and electronic interface, e.g., the data input module described above with respect to FIGS. 5-7, to automatically adjust to the desired height and horizontal offset for the user. For example, the vertical and horizontal adjustment may be automated and controlled by a hydraulic piston or similar mechanism. The piston can be controlled by a controller that may have user specific programming stored in a memory such that a user can enter specific height and weight data into the controller, which will then control the pistons to properly adjust the base to accommodate the user. Rather than requiring user input, the base also may have sensors that detect user-specific criteria such as, e.g., height, weight, etc., and adjust the base according to those criteria. The sensors may be pressure sensors, optical sensors, or another sensing device as will be appreciated by one of skill in the art.

Continuing to refer to FIG. 11, the nerve mobilization apparatus 50 has several nerve mobilization tracks extending from the vertical members. The nerve mobilization tracks 54 may be fixed to the back support, to a wall, or to another vertical member. As labeled in FIG. 11, the tracks 54 simulate the appropriate trajectories for mobilizing the ulnar, medial and radial nerves. The mobilization tracks follow predetermined nerve mobilization trajectories U, M, R as described above to mobilize the ulnar, median or radial nerves with the proper movements.

The nerve mobilization tracks may be connected to the back support or vertical members by any conventional securing mechanism or means, for example welds, bolts, or screws, rivets, etc. Alternatively, the nerve mobilization tracks may be hinged to vertical members or back support such that they are foldable relative to the base to facilitate storage of the arm and shoulder mobilizer or to reduce the size of the mobilizer apparatus when it is not in use.

Figure 12:
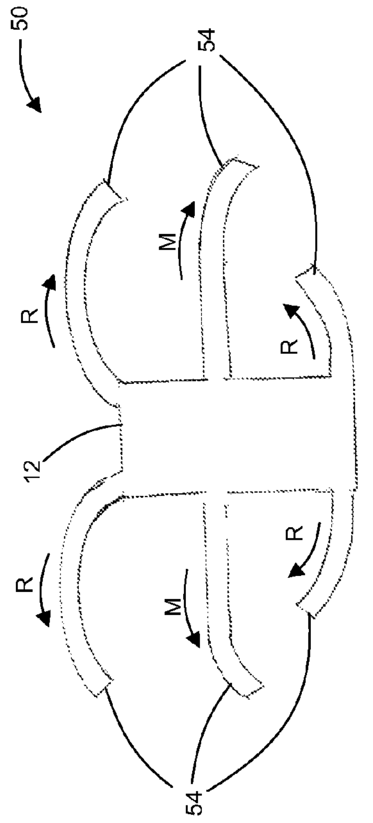
FIG. 12 is a diagrammatic illustration of an upper body nerve treatment apparatus in accordance with a another exemplary embodiment.

Referring briefly to FIG. 12, the arm and shoulder mobilizer tracks 54 may be a stand-alone unit capable of attachment to the nerve treatment apparatus 10 described above. The mobilizer of FIG. 12 may be attached to the rear of the back support of the nerve treatment apparatus 10 to allow both the nerve treatment apparatus 10 and arm and shoulder mobilizer 50 to be utilized as a common piece of equipment.

Rather than mounted to a wall, the nerve mobilization apparatus may be a portable and easily stored apparatus that may be folded in a compact manner to facilitate moving and or storing the nerve mobilization apparatus. The nerve mobilization apparatus also may be attached to or used in conjunction with the neck retractor described above, and may be fixedly attached to the nerve treatment apparatus 10 or attached to a wall, etc.

In one embodiment, the mobilization tracks 54 generally have a U-shape cross-section to slidably engage the gripping implement 56. The gripping implement 56 may be a handle engaged to the tracks in a relatively low friction manner, such as, for example, by ball bearings or the like. As will be appreciated by one of skill in the art, other gripping implements may be used to engage the tracks. For example, rather than sliding on the tracks, the gripping implement may engage rollers contained within or engaged to the tracks, or the gripping implement may be removably positioned in the mobilization track such that the user can easily remove the implement for use with a different mobilizer track.

The gripping implements together with the mobilization tracks also may provide inward and/or outward resistance during the nerve mobilizations. For example, the gripping implement may be attached to a resilient member, such as, for example, a rubber band, exercise stretch band, spring, or the like. The resilient member may be attached to the handle and the base to provide outward resistance during the nerve glide, or may be attached to a distal end of the mobilization track to provide inward resistance during the nerve glide. As described above, the use of a resilient member strengthens the surrounding musculature.

It will be appreciated that the nerve mobilization tracks may be made of a variety of materials and/or be embodied in a variety of configurations without departing from the scope of the present invention. In one embodiment, the back support is coupled to a nerve mobilization track surface, which can be made of any suitable resilient material, such as, for example, Plexiglas, metal, wood, plastic, etc. The nerve mobilization track surface includes or otherwise defines one or more cutaway portions that support and/or guide the handle along the arcuate/curved path, e.g., the nerve mobilization trajectories R, M, U described above. Alternatively, the back support may be coupled to or otherwise associated with a plurality of tubular members configured to provide the nerve mobilization path. In this exemplary embodiment, the handle may be coupled to a sleeve or other connector that slidably/movably couples the handle to the tubular members.

In another embodiment, an adjustable support is disposed on the nerve mobilization track surface. The support is movable to any of a plurality of positions on the surface and is located at a position to support the user's arm during nerve mobilization. For example, the support is located below the arm during medial and ulnar nerve mobilizations such that the user's arm may rest on the support while it is extended. The support also facilitates isolation of the nerves and muscles in the arm, neck and spine, but reducing extraneous use of muscles to keep the arm outstretched. The support may be attached to the surface via a suction cup, screw, pin, or other mechanism. Alternatively, the support may be an adjustable height, stand-alone support having adjustable legs to allow the user to place the support at any desired height or location. It will also be appreciated that the support member may be electronically controlled, for example, by a piston or other mechanism and may automatically move to a preprogrammed or sensed location based upon the specifications of the user.

In another embodiment, the mobilization tracks and gripping implement are electronically controlled by a motor, hydraulic piston, or similar device. The handle may be electronically controlled to slide along the mobilization trajectory to guide a user's arm in the proper positions, for example, if the user's are is particularly weak or if the user is unable to perform the movements without assistance. The electronically controlled handles also may be controlled to provide resistance and/or tension while the user is moving the handles in the tracks to aid in strengthening the musculature surrounding the nerves.

Further, while described with respect to ulnar, medial and radial nerve mobilization, it will be appreciated that it is not necessary for the mobilizer to treat all three nerves, e.g., the mobilizer may treat only the ulnar and radial nerves and may not have a medial nerve trajectory. Additionally, the arm and shoulder mobilizer may be adapted to treat other nerves in the peripheral nervous system without departing from the scope of the present invention.

Figure 14:
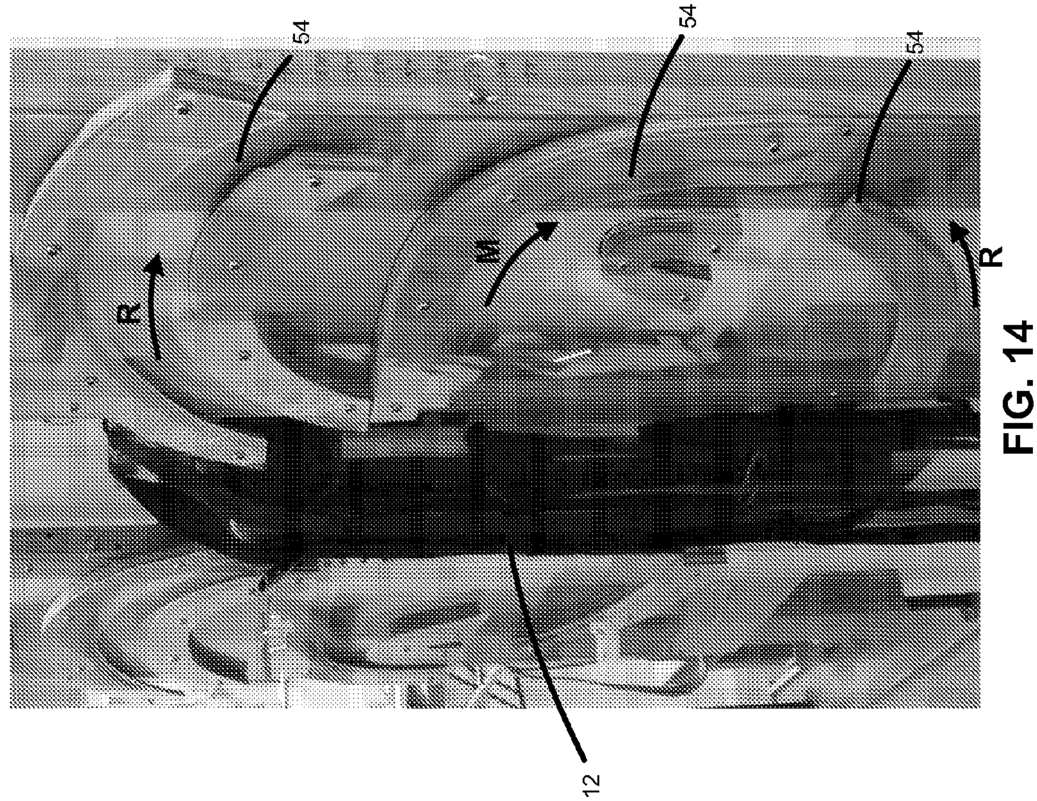
FIG. 14 is a second perspective view of an exemplary upper body nerve treatment apparatus.
Figure 13:
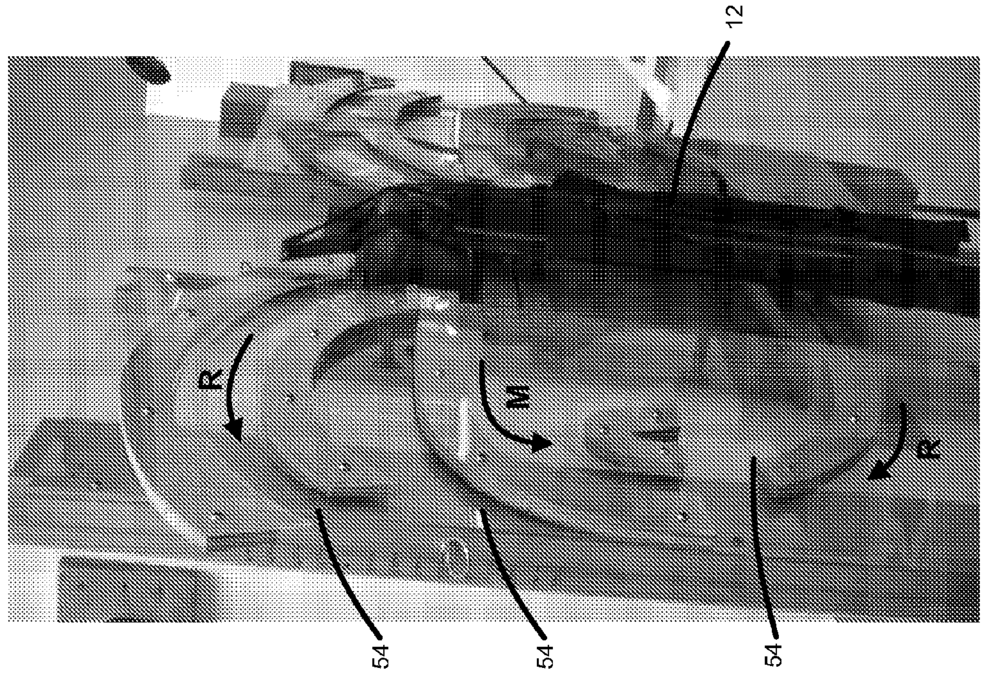
FIG. 13 is a first perspective view of an exemplary upper body nerve treatment apparatus.

FIGS. 13 and 14 are pictorial representations of an exemplary arm and shoulder mobilizer 50. It will be appreciated that the arm and shoulder mobilizer may be configured as an attachment for the above-described nerve treatment apparatus. Alternatively, the arm and shoulder mobilizer may be configured as a stand-alone unit.

Pain in the lower extremities that does not respond to other treatments may be alleviated by mobilizing neural scar tissue that formed at the original site of pain, for example, the nerve at the heel could be caught up in the healing process of Achilles' tendonitis or plantar fascitis.

Referring now to FIGS. 15-21, a lower body nerve treatment apparatus 80 (also referred to as a lower body nerve mobilizer, a lower body peripheral nerve mobilizer, a lower peripheral nerve mobilizer, or a lower body nerve treatment attachment or component) is disclosed. As is discussed below, the lower body nerve treatment apparatus 80 is effective to mobilize peripheral nerves of a user's lower body. By doing so, it is believed that the lower body nerve treatment apparatus will be effective in accomplishing one or more of the following: fixing the lumbar spine in extension for performance of hamstring stretches, focusing the stretch on the proximal hamstrings; positioning the ankle to focus on Achilles' tendon, gastrocnemius and soleus stretch; minimizing resistance for performance of sciatic nerve glides, mobilizing all of the branches of the sciatic and tibial nerves; the stabilization at the hips, e.g., via hip supports or a pelvis fixation member, during the nerve glide eliminates or minimizes the potential of human error in achieving an effective glide; allowing for optimal mobilization of the proximal and distal femoral nerve through the full length of the nerve including the saphenous branch. This may be achieved by allowing the lumbar spine to be stabilized in extension while the hip glides into extension and the knee into flexion. This same movement will also provide an effective quadriceps stretch by avoiding the opportunity for human error in achieving an effective stretch.

Figure 15:
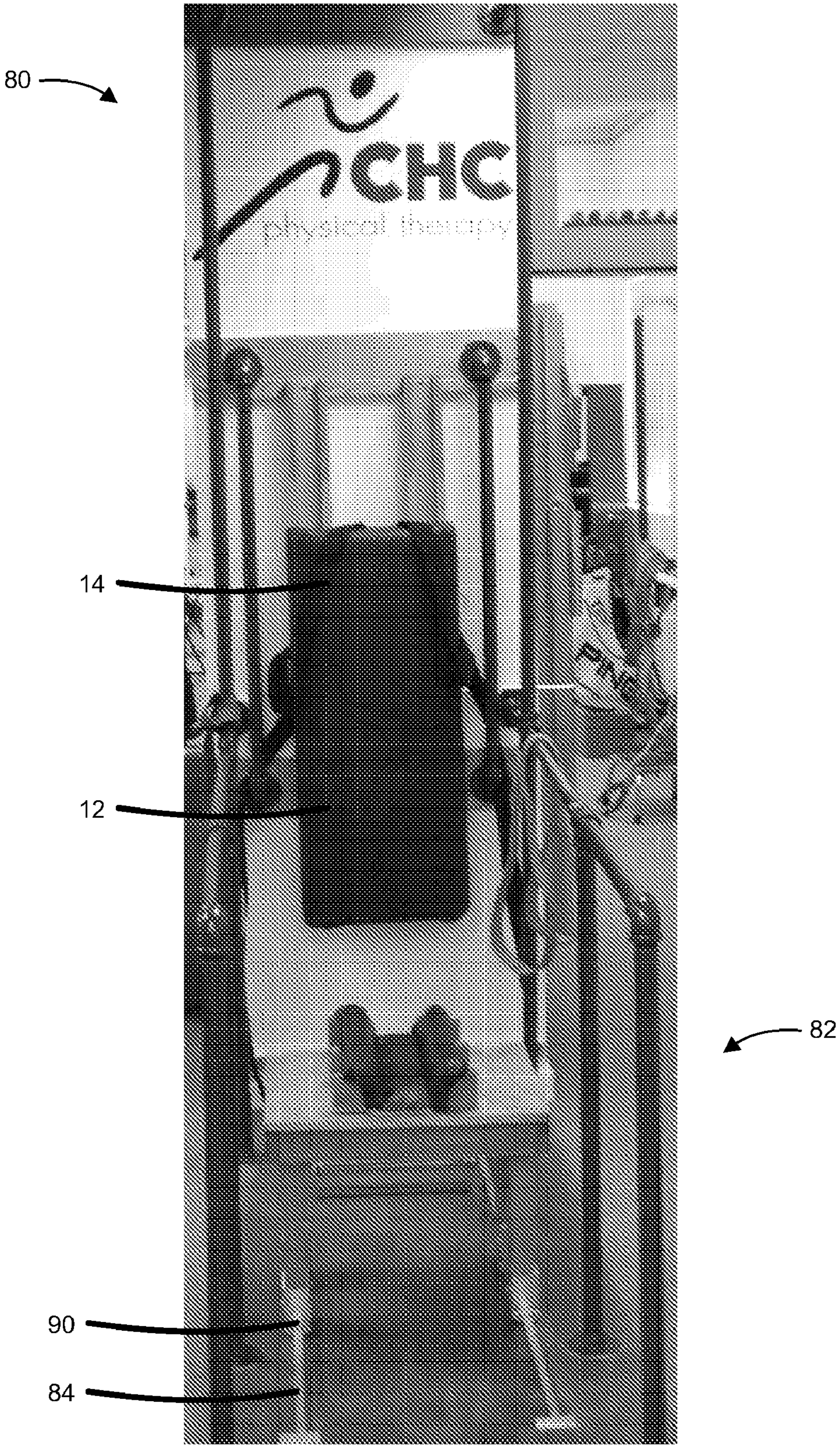
FIG. 15 is a diagrammatic illustration of an exemplary embodiment of a lower body nerve treatment apparatus.

Referring to FIG. 15, the lower peripheral nerve mobilizer 80 includes a back support 12, which, in one embodiment, is the same or similar to the back support described above with respect to the nerve treatment apparatus 12 and the arm and shoulder mobilizer 50. As is described above, the lower peripheral nerve mobilizer may be incorporated into a unitary nerve mobilizer that enjoys the functionality herein described with respect to the nerve treatment apparatus 10, the arm and shoulder mobilizer 50 and the lower peripheral nerve mobilizer 80.

As is discussed above, the back support may include a main support 12, e.g., a back support, that supports the user's back and facilitates, restores and/or increases the lower cervical and/or lumbar spine extension by restoration of the spine curves. As is described above with respect to FIGS. 1-7, the back support may include or otherwise be operatively coupled to a lumbar extension member, e.g., a lumbar roll member. The lumbar extension member may be formed integrally with the back support 12 or, alternatively, the lumbar extension member may be configured as an attachment to the back support 12.

The back support may also include or otherwise cooperate with one or more hip supports that are configured to cooperate with the back support 12 to retain or otherwise support the user's pelvis or hips against the back support 12. Stated differently, the hip supports may be configured to engage the user's anterior iliac crests to retain or otherwise support the user against the back support 12. It will be appreciated that the combination of a back support, equipped with or otherwise operatively coupled to a lumber extension member and a pelvis fixation member, will be effective to facilitate lumbar spine extension for a user of the nerve treatment apparatus.

As is described above with respect to FIGS. 1-7, the main support may be operatively coupled to or otherwise associated with a pair of force applying members, such as, for example, straps or belts or force-applying arms that pull or push the shoulders in the direction of the thoracic muscles, as described above with respect to the nerve treatment apparatus 10. The support or force in the direction of the thoracic muscles also may be provided by an electronically controlled device, such as a hydraulic piston or otherwise as will be appreciated by one of skill in the art. Regardless of how the force is applied, the combination of the back support and force in the direction of the thoracic muscles restores the correct body alignment and in particular, the alignment of the spinal column. It also activates the postural muscles and increases potential vital capacity by maximizing expansion of the rib cage. Furthermore, the back support directs the lumbar curve into extension and flexion and decreases the compressive forces on the anterior aspect of the vertebral bodies in the thoracic spine by decreasing the thoracic spine kyphosis. The back support also promotes passive lumbar spine extension and active lumbar spine flexion. The height of the back support is adjustable to accommodate taller or shorter users.

The lower peripheral nerve mobilizer 80 also has a slidable support or slider 82. The slider is slidable or otherwise movable on a pair of tracks 84 or slider guides that are substantially perpendicular to the back support. In one embodiment, lower peripheral nerve mobilizer has a base apparatus 86, as depicted in FIG. 15. The base 86 is a generally flat shape surface with two handrails attached to the base by a suitable attachment mechanism such as screws, rivets or welds to create a substantially rigid structure for the participant to hold onto for support and balance while using the slider apparatus. The handrails may be formed from wood or metal tubing, and also may have a circular or rectangular cross sectional area. Regardless of the actual shape, each handrail is formed in an ergonomic manner to allow the participant to easily grasp the handrails for support and balance and to allow for the ease of ingress and egress to the mobilizer.

The base member 86 and handrails may be permanently or semi-permanently attached to a wall for further support and rigidity. In the exemplary embodiment where the base member 86 and handrails are attached to the wall, the tracks 84 are generally perpendicular to the wall. Optionally, the participant can then attach a resistance band to a hook on the wall and the slider in order to increase resistance during the exercise as described below.

In the exemplary embodiment depicted in FIG. 15, the base 86 is an elongate member with a substantially flat top surface. The base 86 is preferably a relatively thin rectangular surface, which sits on top of the floor of a gym or other facility. The base 86 may be constructed of any sturdy, solid material, for example, wood, metal, rubber, or other suitable substantially rigid material.

In one embodiment, two tracks 84 are disposed the top surface of the base 86. In the illustrated embodiment, the two tracks 84 are substantially parallel to one another and provide a universal guide for the hip, knee and ankle nerve mobilization exercises.

In one embodiment, the tracks 84 have a substantially U-shape cross section, and are constructed from metal. The tracks 84 may be attached to the top surface by any conventional means including, for example, rivets, screws, adhesive or other suitable attaching materials. In another embodiment the track may be embedded in the top surface of the base member 86 such that the top of the U-shape cross sectional area is substantially even with the top surface. In another embodiment, the tracks are integrated with the floor of the facility such that a separate base is unnecessary. It will be appreciated that greater or fewer than two tracks can be employed without departing from the scope of the present invention.

Figure 16:
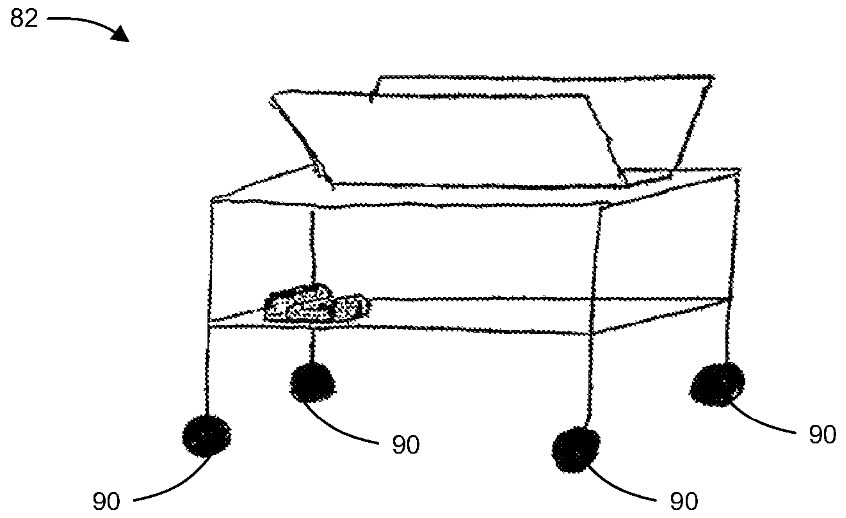
FIG. 16 is a diagrammatic illustration of an exemplary slider associated with the lower body nerve treatment apparatus.

Referring to FIG. 16, an exemplary slider 82 is shown. The slider 82 slidably engages the tracks 84. The slider 82 includes a leg/foot support or leg/foot cradle 88 configured to receive a portion of a user's leg, such as, for example, the heel or the shin, as described below. The movement of the slider facilitates the mobilization of the nerves in the lower peripheral nervous system.

In one embodiment, the slider 82 has a top surface and several supporting legs. Disposed on the top surface of the slider is leg or foot support 88. In the illustrated embodiment, the leg/foot support 88 includes two angled members which form a cradle, e.g., a substantially U-shaped or V-shaped cradle. The support 88 is adapted to support the user's leg or foot during nerve mobilization, and may be padded with, for example, rubber or foam. The support may be permanently or semi-permanently attached to the top surface of the slider by any conventional securing mechanism such as, e.g., screws, rivets, welds, or other securing mechanisms. Furthermore, the slider and leg support may be constructed from wood, metal, plastic, or another suitable material.

With continued reference to FIGS. 15 and 16, the slider 82 includes one or more sliding members 90 that slidably engage to the track 84 to allow or otherwise facilitate a smooth and uninterrupted lateral movement of the slider along the tracks. The sliding members may be conventional casters that fit on the tracks and facilitate the lateral motion of the slider when the mobilizer is in use. It will be appreciated that the sliding members may be any suitable sliding mechanism that facilitates the lateral movement of the slider. It will also be appreciated that other sliding mechanisms besides casters may be used to facilitate sliding or movement of the slider 82 on the tracks 84 by providing a low-friction, low-resistance means for sliding the slider 82. For example, the sliding members may be low friction pads or, alternatively, a series of ball bearings may be disposed on the interior of the track for engagement to a lower portion of the legs on the slider. The sliders also may be easily inserted and removed from the tracks so as to allow the user to easily interchange sliders as desired.

Optionally the slider also may be coupled to a resistance member such as, for example, a rubber exercise band. The resistance member increases resistance to the lateral movement of the cart during use. In use, the resistance member may be attached to the slider 82 and the wall via hooks. Alternatively, the resistance band or other resistance member may be hidden from view and disposed beneath or within the tracks and attached to the legs of the slider rather than to a hook. It will be appreciated by one skill in the art that the elastic band may be eliminated or replaced as desired and that different sized bands may be selected to give the user more or less resistance.

In another embodiment, the lower peripheral nerve mobilizer 80 is automated such that the lateral movement of the slider is electronically controlled. The electronic control may be a programmable, electronic controller, piston, motor, etc., that automatically controls the lateral movement of the slider. The electronic controller also can be programmed or adjusted to provide mechanical resistance to the movement of the slider while the mobilizer is in use.

In one embodiment the slider is approximately 18" in height and constructed from a durable metal such as, for example, aluminum or stainless steel. Alternatively, the slider may be formed from a plastic or other material. It will also be appreciated that the height of the cart may be greater or less than 18" depending upon the size participant's height. Alternatively, the height of the slider may be adjustable to accommodate different size users.

In one exemplary embodiment, the lower peripheral nerve mobilizer may include a movable, e.g., a telescoping, ankle glider implement that is configured to engage a portion of the user's leg or foot in a manner consistent with that described below with respect to FIGS. 20 and 21.

It will be appreciated that the lower peripheral nerve mobilizer may be configured as an attachment for the above-described nerve treatment apparatus 10. Alternatively, the lower peripheral nerve mobilizer may be configured as a stand-alone unit.

Figure 17:
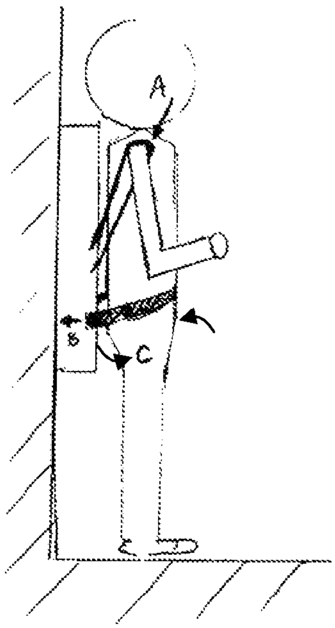
FIG. 17 illustrates a user performing a posterior pelvic tilt on an exemplary embodiment of the lower body nerve treatment apparatus.

Referring to FIG. 17, an exemplary embodiment of the lower peripheral nerve mobilizer is shown. In one embodiment, the user's back is adjacent to and in contact with the back support 12. As described above, the back support 12 is configured with straps or other suitable force applying members (such as those described above with respect to FIGS. 1-7) to exert force in the direction of the lower thoracic muscles to restore correct body alignment and isolate the spinal column, as shown at A on FIG. 17. A second belt or strap (also referred to as a pelvis fixation member, a pelvis retention member a hip support or the like) is also secured around the lower torso or waist of the user to assist in the isolation of the spine and to support/secure the user's body against the back support. In the illustrated embodiment, the second belt is a rubber strap or resistance strap that aids in stabilizing the spine. The combination of the securing/strapping mechanisms facilitates activation of the core in a standing posture and provides feedback that the core is activated during exercise of the upper and lower extremities. As already described in detail, the forces and resistances provided by the straps can be provided by mechanically or electrically controlled mechanisms. Optionally, a separate adjustable strap may be employed.

FIG. 17 is exemplary of the lower peripheral nerve mobilizer used to perform a posterior pelvic tilt. The posterior pelvic tilt mobilizes, activates and exercises the lower abdominal muscles. As described above, the back support stabilizes the spinal column to maintain and/or facilitates the curve of the spine and proper posture of the user. As described above, a force A is supplied to the user's shoulders along the line of the thoracic muscles. A second force B is supplied to the user's waist or across the user's hips to further stabilize the spinal column. The second force B may be in the form of a strap or belt across or around the user's lap, hips, or waist. The strap may be flexible and/or stretchable to provide resistance to movements of the user's hips and/or lower torso.

As described with respect to the lower peripheral nerve mobilizer and as described herein, the use of the back support also minimizes resistance for performing sciatic nerve glides and assists to mobilize all of the branches of the sciatic and tibial nerves. The stabilization at the hips by the mobilizer during the nerve glides/mobilizations also eliminates or at least minimizes the potential of human error in achieving an effective mobilization. The back support also allows for optimal mobilization of the proximal and distal femoral nerve through the full length of the nerve including the saphenous branch. This is achieved by stabilizing the lumbar spine in extension while the hip glides into extension and the knee into flexion. This same movement will also provide the optimal quadriceps stretch by avoiding the opportunity for human error in achieving an effective stretch.

As illustrated in FIG. 17, the user performs the posterior pelvic tilt using the mobilizer. The posterior pelvic tilt is a core exercise/movement performed by moving/rotating the pelvis along the general direction marked C in FIG. 17. The lower pelvis, e.g., the tailbone and buttocks are rotated forward or away from the back support, while the lower abdomen is rotated/moved towards the back support. By moving/rotating the pelvis while using the back support to stabilize the spine and torso, the user is forced to use the lower abdominals hold the lower back and tilt the pelvis.

While performing the posterior pelvic tilt, the user's core and lower abdomen are activated, and the user can exercise other parts of the body, for example, the upper extremities can be exercised by performing, for example, bicep curls, triceps exercises or other upper extremity exercises. The user also can perform lower extremity exercises, for example hamstring, quadriceps or calf muscle exercises, etc. These exercises can be further facilitated by attaching weights or elastic exercise bands to the mobilizer apparatus or slider, to provide resistance during the exercise.

Figure 18:
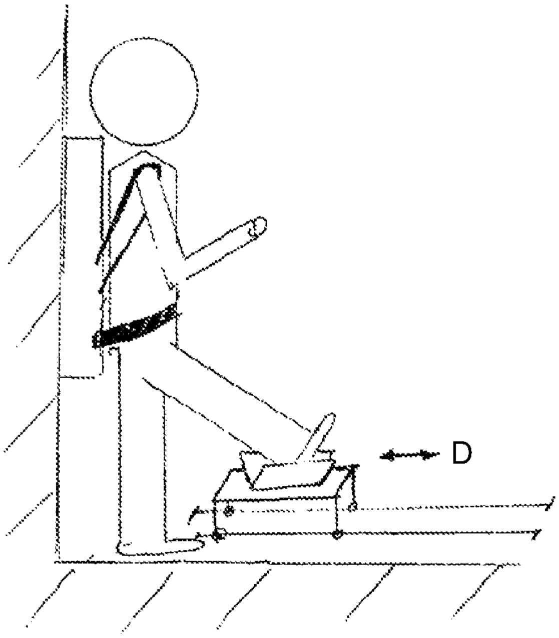
FIG. 18 illustrates a user performing hamstring glide on an exemplary embodiment of the lower body nerve treatment apparatus.
Figure 25:
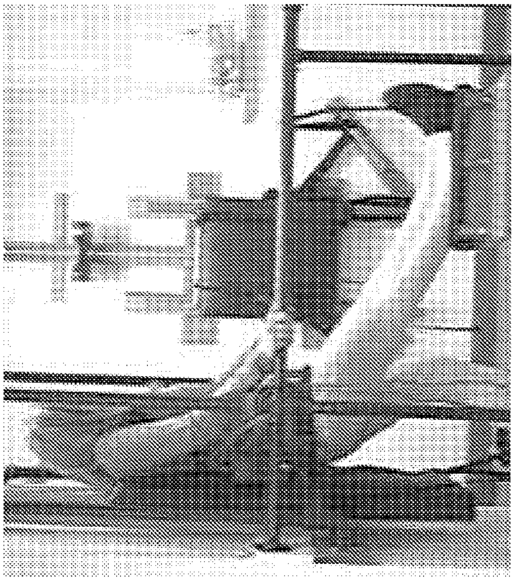
FIG. 25 illustrates a user performing hamstring glide on an exemplary embodiment of the lower body nerve treatment apparatus.

As shown in FIGS. 18 and 25, the mobilizer is used to stretch the hamstring muscle and mobilize the nerves in the lower peripheral nervous system, such as, for example, the sciatic and/or or tibial nerves. Using the back support and force applying members, as described in detail above, the mobilizer maintains the curve of the spine by providing lumbar support. The mobilizer also has a waist strap, to hold the hips against the back support. Also, as is described above, the mobilizer may include a separate adjustable strap.

The user rests one foot in the slider, and, while keeping one leg stationary on the floor and the other leg generally straight and on the slider, the user moves the slider along the tracks in direction D. The movement of the slider, while maintaining the back with the back support isolates the hamstring of the leg on the slider and focuses the stretch on the proximal and distal hamstring muscles while maintaining the lumbar spine curve. In other words, the mobilizer fixes the lumbar spine in extension for performance of hamstring stretches, focusing the stretch on the proximal and distal hamstrings. The mobilizer and slider also such that an extension can be placed on the slider to focus stretches on Achilles tendon, gastrocnemius and soleus muscles.

Figure 19:
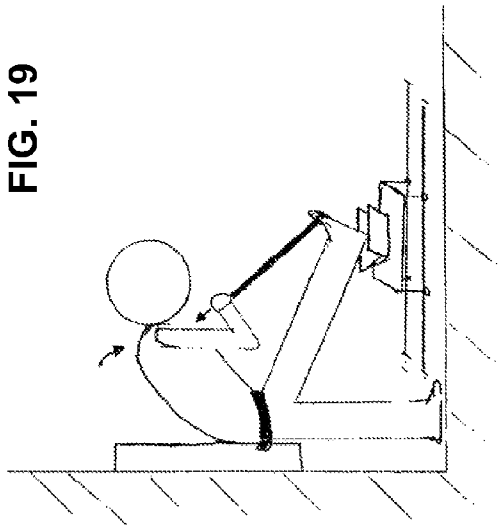
FIG. 19 illustrates a user performing a modified slump on an exemplary embodiment of the lower body nerve treatment apparatus.
Figure 20:
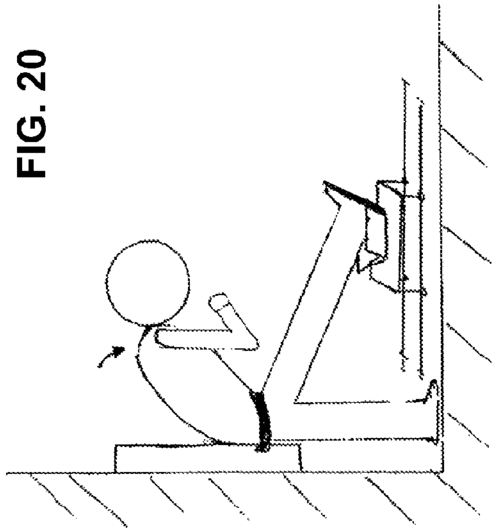
FIG. 20 illustrates a user performing a modified slump on an exemplary embodiment of the lower body nerve treatment apparatus.
Figure 26:
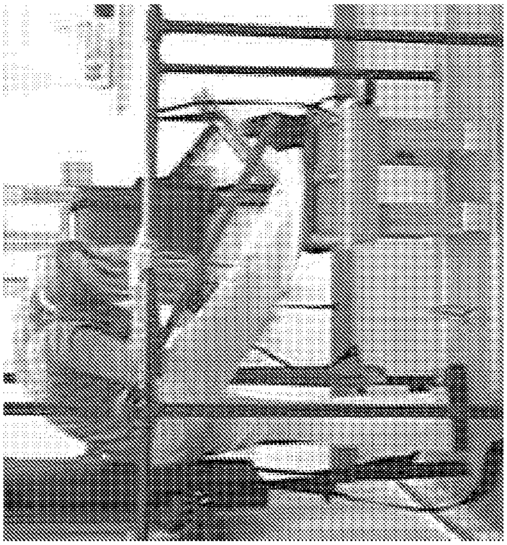
FIG. 26 illustrates a user performing a modified slump on an exemplary embodiment of the lower body nerve treatment apparatus.

Referring to FIGS. 19, 20 and 26, the nerves in the lower extremities are mobilized by placing a resistance band or elastic band around the ball of the foot. In particular this stretch or glide minimizes slack in the central and peripheral nervous systems and mobilizes the sciatic nerve. The user enters the mobilizer without the force applying members. With the lower back against the back support, the user slumps forward and holds onto the elastic band with the hands. When the user flattens the back and pulls the resistance band towards the shoulders, the entire nervous system, e.g., the nerves that travel from the brain to the toes, are addressed and mobilized. The stretch/exercise is also referred to as a modified slump and may be used to alleviate or relive heel pain and/or compression in the nerves of the lower peripheral nervous system.

In another embodiment, illustrated in FIG. 20, rather than, or in addition to the stretch band a support, e.g., a padded, adjustable support, may be attached to the slider. The adjustable support lifts and holds the ankle at a suitable angle, e.g., approximately a 90-degree angle or at the maximum dorsi flexion achievable by the user.

Figure 21:
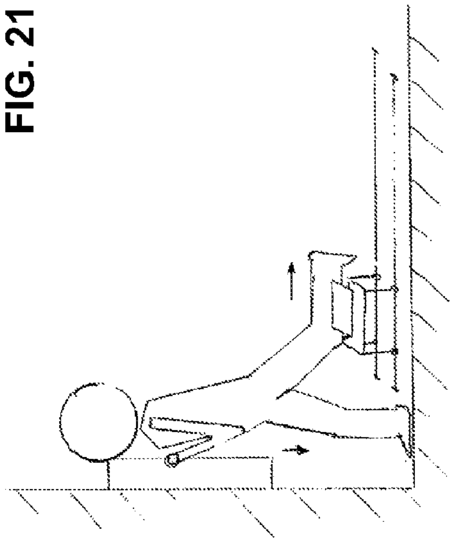
FIGS. 21-24 illustrate a user performing a hip slide on an exemplary embodiment of the lower body peripheral nerve mobilizer.
Figure 22:
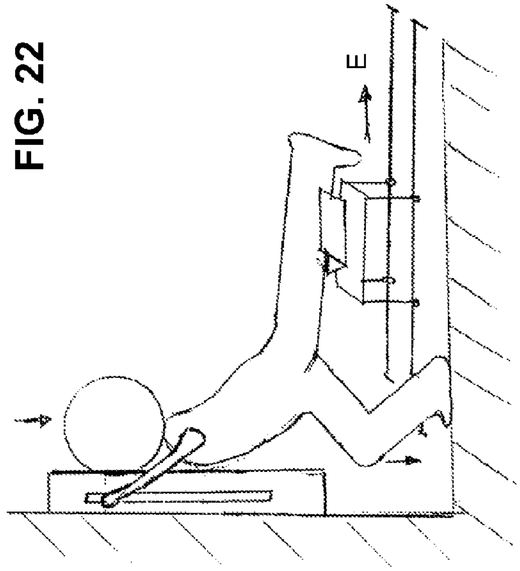
Figure 27:
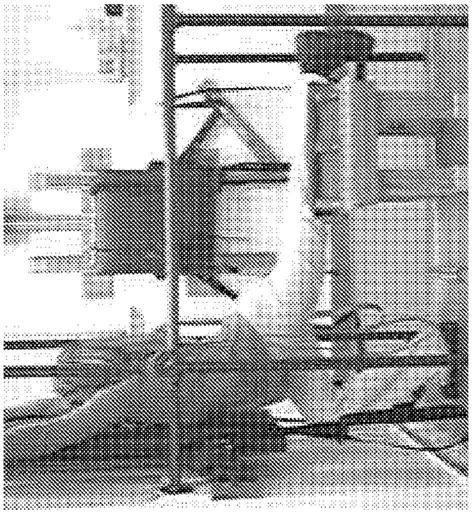
FIG. 27 illustrates a user performing a femoral nerve glide on an exemplary embodiment of the lower body peripheral nerve mobilizer.

Referring now to FIGS. 21-22 and 27, the lower peripheral nerve mobilizer is shown as used to extend, stretch and/or mobilize the hip and mobilize/glide the femoral nerve. When used to mobilize/extend the hips, the user faces the back support, as shown in FIGS. 21-22 and 27. The back support may have a handle, bar or other gripping mechanism for the user to grasp while the mobilizer is in use as shown. Although shown as a bar, it will be appreciated that any convention gripping mechanism may be utilized, including mechanical or automated gripping mechanisms, etc.

The user places the leg into the slider such that the tibia or the front of the lower leg rests in the support while the other leg remains stationary on the floor. The user then performs a lunge-like motion by bending the knee of the stationary leg and extending the leg in the slider, such that the slider moves along the tracks in direction E. When performing the lunge or lunge-like motion, the back is arched and the hip is extended and stretched. This movement stretches the quadriceps muscle and mobilizes the nerves in the lower peripheral nervous system. This movement also encourages maximum lumbar curve while gliding the femoral nerve into its end range of movement. In other words, the lumbar spine is extended while the hip glides into extension and the knee into flexion. This same movement may also be effective to provide a beneficial quadriceps stretch by avoiding the opportunity for human error in achieving an effective stretch.

Figure 24:
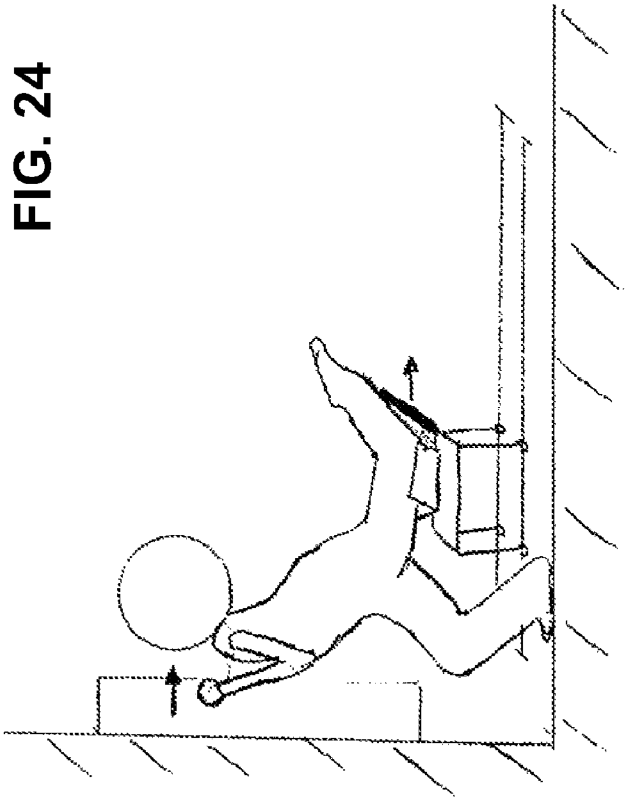
Figure 23:
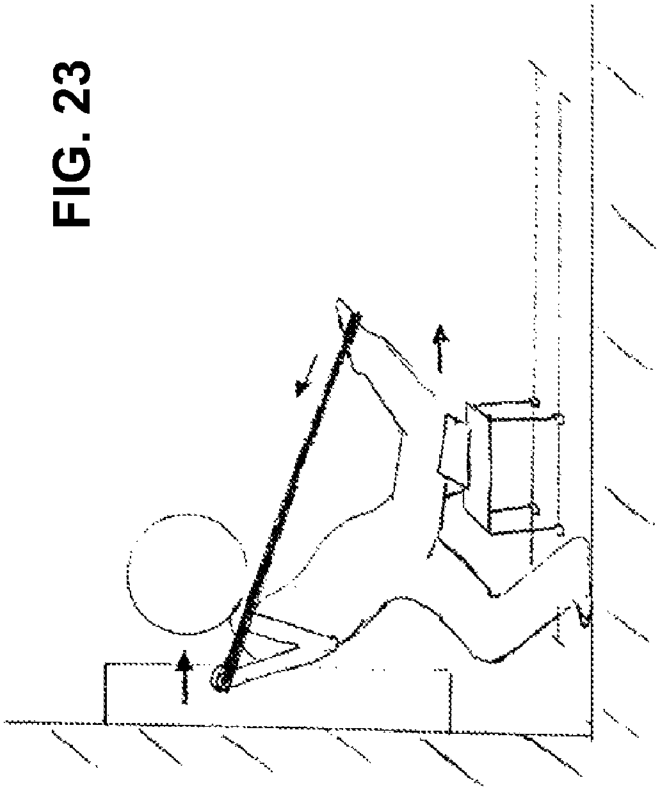

As shown in FIGS. 23-24, this stretch/movement can be further performed using a resistance band wrapped around the user's foot and held by the user's hand. As shown, the user arches the back and pulls the resistance band while performing the lunge described in FIGS. 21-22 and 26. This movement further facilitates the mobilization of the nerves in the lower peripheral nervous system and stretches the muscles in the back and legs, and in particular, the quadriceps muscles.

In another embodiment, illustrated in FIG. 24, rather than, or in addition to the stretch band, a padded, adjustable support is attached to the slider. The adjustable support lifts and holds the leg to facilitate the movement described above.

Although described with respect to mechanical structures and manual movements by the user, it will be appreciated, as described above, that the movements, stretches, extensions and mobilizations described above may be performed with an automated apparatus, which may be programmed to meet the user's specific criteria and/or needs, and may include a programmable controller, motor, pistons and sensors to effectively and safely perform the movements described herein.

As is described more fully below, the peripheral nerve mobilization facilitated by the nerve treatment apparatus (or apparatuses) described above is believed to have a number of practical applications and benefits to users. For example, the nerve treatment apparatus (or apparatuses) is effective to facilitate mobilization of the proximal neural structures. In addition, the nerve treatment apparatus (or apparatuses) assist in directing movement of the cervical and lumbar spine into extension—posterior convex spinal curve. Other benefits include, but are not limited to, restoring a user's correct body alignment, correcting or otherwise treating neck stiffness, pain and/or alignment that can contribute to poor body alignment, minimizing the loss of height, or maximizing the potential to restore height loss.

Other intended benefits of the nerve treatment apparatus (or apparatuses) include improved movement of the user's entire body, decrease or elimination of pain if it is present, including, arthritis pain, elbow pain, shoulder pain, “pins and needles” in the arms or hands, when, e.g., reading, biking, using a computer, repetitive movements and static movements such as drying hair and driving, restoring head/neck rotation and the like; activation of the lower trapezius muscle, and inhibiting the antagonist pectoralis muscle, thereby allowing for an effective stretch. Also, as is described more fully below, the peripheral nerve mobilization facilitated by the nerve treatment apparatus (or apparatuses) is believed to be effective in treating and/or training sports-related motions, work-related motions, correcting forward shoulder and/or forward head posture in an individual, remodeling neural scar tissue, treating pain in an individual's upper/lower extremities, increasing vital capacity by maximizing the expansion of the rib cage, activating postural muscles, restores correct body alignment, promoting passive lumbar spine extension and active lumber spine flexion, facilitating activation of the core in a standing posture, and providing feedback that the core is activated during exercise of the upper and lower extremities, and the like.

The nerve treatment and/or mobilization apparatus(es) herein described may be employed in connection with a variety of practical applications, including, but not limited to, treating limitations in connection with treating a user's sports-related and/or work-related motions; correcting a user's forward head and/or forward shoulder posture; remodeling a user's neural scar tissue; treating pain in an individual's upper extremities; and treating pain in an individual's lower extremities. These treatment methods may be carried out by mobilizing all or part of an individual's peripheral nervous system using one or all of the nerve treatment apparatus 10, the upper body nerve mobilization apparatus 50 and/or the lower peripheral nerve mobilization apparatus 80. Of course, as is discussed above, the functionality of each of apparatuses 10, 50 and 80 may be embodied in a single nerve treatment/mobilization apparatus (e.g., nerve treatment apparatus 10, including attachments corresponding to nerve mobilization apparatuses 50 and 80).

Other potential benefits may include rehabilitation of severe burns and the remodeling of the scar tissue. Scar tissue formation is part of the healing process and the nerve treatment/mobilization apparatus(es) 10, 50 and/or 80 are believed to be effective in maintaining movement during this process. As the burn becomes chronic, scar tissue continues to shorten. The nerve treatment/mobilization apparatus(es) 10, 50 and/or 80 will prevent additional loss of movement.

The nerve treatment/mobilization apparatus(es) 10, 50 and/or 80 are believed to be effective in addressing pain in the upper extremities including the shoulder, elbow and wrist pain which does not respond to other treatments. This is accomplished by mobilizing neural scar tissue that formed at the original site of pain, for example, the nerve at the elbow could be caught up in the healing process of a tendonitis. Carpal tunnel syndrome can be exacerbated by incorrect mobilizations.

While for purposes of simplicity of explanation, the methods discussed herein include a series of steps, events or functional blocks that represent one or more aspects of the relevant operation of the disclosed training and treatment method(s), it is to be understood and appreciated that aspects of the invention described herein are not limited to the order of steps, events or functional blocks, as some steps, events or functional blocks may, in accordance with aspects of the present invention, occur in different orders and/or concurrently with other steps, events or functional blocks from that shown or described herein. Moreover, not all disclosed steps, events or functional blocks of aspects of relevant operation may be required to implement a methodology in accordance with an aspect of the invention. Furthermore, additional steps, events or functional blocks representative of aspects of relevant operation of the disclosed training and treatment method(s) may be added without departing from the scope of the present invention.

A method of treating an individual relating to a sports-related and/or work-related motion, the method comprising:

assessing an individual's range of motion with respect to a given sports-related and/or work-related motion;

identifying limitations in the individual's range of motion; and selectively mobilizing portions of the individual's peripheral nervous system based on the identified limitations in the individual's range of motion.

The above method of treating may be described by the step of selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

A method of improving an individual's vital capacity, the method comprising:

selectively mobilizing portions of the individual's peripheral nervous system.

The above method of improving may be described by the step of selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

A method of correcting forward should and/or forward head posture in an individual, the method comprising:

selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

A method of remodeling neural scar tissue in an individual, the method comprising:

selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

A method of treating pain in an individual's upper extremities, the method comprising:

selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

A method of treating pain in an individual's lower extremities, the method comprising:

selectively mobilizing portions of the peripheral nervous system including mobilizing portions of the peripheral nervous system using the herein described nerve treatment apparatus 10, nerve mobilization apparatus 50 and/or lower peripheral nerve mobilization apparatus 80.

Although the invention has been shown and described with respect to certain illustrated embodiment, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiments of the invention.

The invention claimed is:

1. A nerve treatment apparatus comprising:

a back support;

a pair of force applying members movable with respect to the back support, wherein the force applying members are configured to apply forces to a user along predefined directions causing movement of the user's scapulae; and a neck cradle member configured to move concurrently with the force applying members with respect to the back support, the neck cradle member being configured to movably engage a user substantially adjacent the user's occiput and configured to slide up the user's occiput to facilitate retraction of the user's cervical spine.

2. The nerve treatment apparatus of claim 1, further comprising at least one nerve mobilization track operatively coupled to the back support.

3. The nerve treatment apparatus of claim 2, wherein the nerve mobilization track is a radial nerve mobilization track.

4. The nerve treatment apparatus of claim 2, wherein the nerve mobilization track is a median nerve mobilization track.

5. The nerve treatment apparatus of claim 2, wherein the nerve mobilization track is an ulnar nerve mobilization track.

6. The nerve treatment apparatus of claim 2, wherein the at least one nerve mobilization track includes a radial nerve mobilization track, a median nerve mobilization track and an ulnar nerve mobilization track.

7. The nerve treatment apparatus of claim 1, further comprising a safety release mechanism operable to trigger release of force applying members.

8. The nerve treatment apparatus of claim 7, wherein the safety release mechanism includes a release trigger device operable by the user.

9. The nerve treatment apparatus of claim 7, further comprising one or more force sensors operable to sense force and operable to trigger release of the force applying members and the fixation device and the neck cradle upon sensing of predefined force.

10. The nerve treatment apparatus of claim 1, further comprising a lower body slider that is movable in a direction substantially perpendicular to the back support.

11. The nerve treatment apparatus of claim 10, wherein the lower body slider is configured to slide on at least one slider track.

12. The nerve treatment apparatus of claim 10, wherein the lower body slider includes a lower body cradle.

13. The nerve treatment apparatus of claim 1, further comprising at least one motor operatively coupled to the force applying members, a motor controller for controlling the at least one motor and a data entry module configured to receive data relating to the user.

14. The nerve treatment apparatus of claim 13, wherein the data entry module is configured to receive data relating the user's height, weight, age and/or physical condition.

15. The nerve treatment apparatus of claim 1, wherein the force applying members are configured to apply forces adjacent the user's anterior humeral heads.

16. The nerve treatment apparatus of claim 1, wherein the force applying members are configured to apply forces in directions along the user's lower trapezes muscle fibers.

17. The nerve treatment apparatus of claim 1, wherein the force applying members are configured to apply forces effective to activate the user's lower trapezes muscles.

18. The nerve treatment apparatus of claim 1, wherein the force applying members are configured to apply forces adjacent the user's anterior shoulder areas, each of the force applying members being configured to apply a force in a direction having an angle of about 45 degrees with respect to the back support and an angle of about 45 degrees relative to a vertical plane that is perpendicular to the back support.

19. The nerve treatment apparatus of claim 1, wherein the force applying members are configured to apply forces substantially adjacent the user's anterior shoulder areas the forces being directed along an interior, posterior direction of about 45 degrees.

20. The nerve treatment apparatus of claim 1, wherein the force applying members are configured to apply forces effective to facilitate a posterior, inferior glide of the subject's scapulae.

21. The nerve treatment apparatus of claim 1, wherein the force applying members are configured to apply forces in directions effective to facilitate movement of the user's scapulae in a retracted inferior glide.

22. The nerve treatment apparatus of claim 1, wherein the force applying members are configured to intermittently apply forces to the user along predefined directions.

23. The nerve treatment apparatus of claim 1, wherein the force applying members are configured to automatically apply forces to the user adjacent the user's anterior shoulder area along predefined directions.

24. The nerve treatment apparatus of claim 1, wherein the force applying members are operatively coupled to a motor and a motor control, such that the force applying members are operative to automatically apply force to the user along predefined directions.

25. The nerve treatment apparatus of claim 1, wherein the force applying members and the neck cradle member are height-adjustable.

26. The nerve treatment apparatus of claim 1, wherein the force applying members are driven intermittently via an actuation mechanism.

27. The nerve treatment apparatus of claim 1, wherein the back support is configured to direct the user's lumbar spine into extension.

28. The nerve treatment apparatus of claim 1, wherein the back support includes a lumbar roll member.

29. The nerve treatment apparatus of claim 1, further comprising a fixation member configured to cooperate with the back support to retain the user's pelvis against the back support.

30. The nerve treatment apparatus of claim 1, further comprising a hip support configured to retain the user's pelvis against the back support.

31. The nerve treatment apparatus of claim 1, further comprising a retention member configured to engage the user's anterior iliac crests and to retain the user against the back support.

32. The nerve treatment apparatus of claim 1, further comprising a lumber extension device configured to cooperate with the back support to direct the user's lumbar spine into extension.

33. The nerve treatment apparatus of claim 1 , wherein the lumbar extension device comprises a lumbar support member coupled to the back support and a pelvis retention member configured to releasably engage the user's anterior iliac crests.

34. A nerve treatment apparatus comprising:

a back support;

a pair of force applying members movable with respect to the back support, wherein the force applying members are configured to apply forces to a user along predefined directions; and a neck cradle member movable with respect to the back support, the neck cradle member being configured to movably engage a user substantially adjacent the user's occiput and configured to slide up the user's occiput to facilitate retraction of the user's cervical spine;

wherein the force applying members are configured to apply forces adjacent the user's anterior humeral heads, each of the force applying members being configured to apply a force in a direction having an angle of about 45 degrees with respect to the back support and an angle of about 45 degrees relative to a vertical plane that is perpendicular to the back support.

35. A nerve treatment apparatus comprising:

a back support;

a pair of force applying members movable with respect to the back support, wherein the force applying members are configured to intermittently apply forces to a user along predefined directions; and a neck cradle member movable with respect to the back support, the neck cradle member being configured to movably engage a user substantially adjacent the user's occiput and to facilitate retraction of the user's cervical spine;

wherein the force applying members are configured to apply forces effective to direct the user's lower cervical curve into extension and the user's upper cervical curve into flexion.

* * * * *